US012702657B2

(12) United States Patent
Goethals et al.

(10) Patent No.: US 12,702,657 B2
(45) Date of Patent: Aug. 11, 2026

(54) TREATMENT AND PREVENTION OF DENGUE DISEASE

(71) Applicants: Janssen Pharmaceuticals, Inc., Titusville, NJ (US); Katholieke Universiteit Leuven, Leuven (BE)

(72) Inventors: Olivia Gabriella M. Goethals, Bonheiden (BE); Bart Rudolf Romanie Kesteleyn, Berlare (BE); Bart Henri Theresia Stoops, Wechelderzande (BE); Jean-François Bonfanti, Ande (FR); Tim Hugo Maria Jonckers, Heist op den Berg (BE); Marnix Van Loock, Begijnendijk (BE); Suzanne Kaptein, Maastricht (NL); Johan Neyts, Kessel-Lo (BE)

(73) Assignee: Katholieke Universiteit Leuven, Leuven (BE)

( * ) Notice: Subject to any disclaimer, the term of this patent is extended or adjusted under 35 U.S.C. 154(b) by 1007 days.

(21) Appl. No.: 17/777,019

(22) PCT Filed: Nov. 13, 2020

(86) PCT No.: PCT/EP2020/082102

§ 371 (c)(1),
(2) Date: May 14, 2022

(87) PCT Pub. No.: WO2021/094563

PCT Pub. Date: May 20, 2021

(65) Prior Publication Data

US 2022/0409583 A1 Dec. 29, 2022

(30) Foreign Application Priority Data

Nov. 15, 2019 (EP) .................................... 19209593
Dec. 5, 2019 (EP) .................................... 19213851
Apr. 23, 2020 (EP) .................................... 20171172

(51) Int. Cl.
*A61K 31/4045* (2006.01)
*A61P 31/14* (2006.01)

(52) U.S. Cl.
CPC .......... *A61K 31/4045* (2013.01); *A61P 31/14* (2018.01)

(58) Field of Classification Search
CPC .................................................. A61K 31/4045
See application file for complete search history.

(56) References Cited

U.S. PATENT DOCUMENTS 7,601,735 B2 10/2009 Tyms et al.
8,143,259 B2 3/2012 Colburn et al.
8,299,056 B2 10/2012 Bahmanyar et al.
8,324,217 B2 12/2012 Colburn et al.
8,524,764 B2 9/2013 Canales et al.
8,884,030 B2 11/2014 Canales et al.
8,993,604 B2 3/2015 Byrd et al.
9,029,376 B2 5/2015 Byrd et al.
9,522,923 B2 12/2016 Richards et al.
9,944,598 B2 4/2018 Kesteleyn et al.
10,029,984 B2 7/2018 Kesteleyn et al.
10,064,870 B2 9/2018 Rajagopalan et al.
10,071,961 B2 9/2018 Vandyck et al.
10,117,850 B2 11/2018 Griffioen et al.
10,206,902 B2 2/2019 Kesteleyn et al.
10,323,026 B2 6/2019 Ikeda et al.
2005/0239821 A1 10/2005 Neyts et al.
2006/0194835 A1 8/2006 Dugourd et al.
2006/0211698 A1 9/2006 Botyanszki et al.
2008/0318338 A1 12/2008 Kamal et al.
2010/0048589 A1 2/2010 Colburn et al.
2012/0136006 A1 5/2012 Colburn et al.
2013/0023532 A1 1/2013 Casillas et al.
2014/0213586 A1 7/2014 Bardiot et al.
2016/0297810 A1 10/2016 Bardiot et al.
2017/0002006 A1 1/2017 Corte et al.
2017/0096429 A1 4/2017 Corte et al.
2017/0281633 A1 10/2017 Boylan et al.
2017/0281766 A1 10/2017 Wiltzius
2017/0283500 A1 10/2017 Wiltzius et al.
2017/0298017 A1 10/2017 Kesteleyn et al.
2018/0256544 A1 9/2018 Kesteleyn et al.
2018/0256545 A1 9/2018 Kesteleyn et al.
2018/0346419 A1 12/2018 Kesteleyn et al.
2019/0104738 A1 4/2019 Narine et al.

(Continued)

FOREIGN PATENT DOCUMENTS

CN 102026992 A 4/2011
CN 102186833 A 9/2011
CN 104024223 A 9/2014

(Continued)

OTHER PUBLICATIONS

Satoshi Kutsuna, Dengue fever, Infectious Diseases Quick Reference (Kansensyo Quick Reference), 2019 (Well-known art) (Japanese document).

(Continued)

*Primary Examiner* — John S Kenyon
(74) *Attorney, Agent, or Firm* — ICE MILLER LLP

(57) ABSTRACT

The present invention relates to the use of substituted indole derivatives and substituted indoline derivatives in the manufacture of a medicament for the treatment of dengue disease in an individual infected by dengue virus or the prevention of dengue disease in an individual at risk of being infected by Dengue virus. The invention further provides a method for the treatment or the prevention of dengue in an individual at risk of being infected by Dengue virus.

16 Claims, 22 Drawing Sheets

(56) References Cited

U.S. PATENT DOCUMENTS

| | | | |
|---|---|---|---|
| 2019/0112266 A1 | 4/2019 | Kesteleyn et al. |
| 2019/0183931 A1 | 6/2019 | Bakker et al. |

FOREIGN PATENT DOCUMENTS

| | | | |
|---|---|---|---|
| JP | 2012206959 A | 10/2012 |
| JP | 2014527978 A | 10/2014 |
| JP | 2017531619 A | 10/2017 |
| JP | 2017531638 A | 10/2017 |
| JP | 2018503642 A | 2/2018 |
| JP | 2018515495 A | 6/2018 |
| WO | 1999021559 A1 | 5/1999 |
| WO | 2001060826 A2 | 8/2001 |
| WO | 2002089780 A2 | 11/2002 |
| WO | 2003050295 A2 | 6/2003 |
| WO | 2005095403 A2 | 10/2005 |
| WO | 2006071618 A1 | 7/2006 |
| WO | 2006076529 A1 | 7/2006 |
| WO | 2006136305 A1 | 12/2006 |
| WO | 2007017093 A1 | 2/2007 |
| WO | 2007026920 A2 | 3/2007 |
| WO | 2009149054 A1 | 12/2009 |
| WO | 2010021878 A1 | 2/2010 |
| WO | 2010027500 A1 | 3/2010 |
| WO | 2010091413 A1 | 8/2010 |
| WO | 2011031669 A1 | 3/2011 |
| WO | 2011037643 A2 | 3/2011 |
| WO | 2011088303 A1 | 7/2011 |
| WO | 2011120025 A1 | 9/2011 |
| WO | 2013045516 A1 | 4/2013 |
| WO | 2014154682 A1 | 10/2014 |
| WO | 2015187815 | 12/2015 |
| WO | 2015188009 | 12/2015 |
| WO | 2016050831 A1 | 4/2016 |
| WO | 2016050841 A1 | 4/2016 |
| WO | 2016053455 A1 | 4/2016 |
| WO | 2016057905 | 4/2016 |
| WO | 2016113371 A1 | 7/2016 |
| WO | 2016180696 A1 | 11/2016 |
| WO | 2017013265 | 1/2017 |
| WO | 2017046255 A1 | 3/2017 |
| WO | 2017046258 A1 | 3/2017 |
| WO | 2017079216 A1 | 5/2017 |
| WO | 2017165736 A1 | 9/2017 |
| WO | 2017167832 A1 | 10/2017 |
| WO | 2017167950 A1 | 10/2017 |
| WO | 2017167951 A1 | 10/2017 |
| WO | 2017167952 A1 | 10/2017 |
| WO | 2017167953 A1 | 10/2017 |
| WO | 2017171100 A1 | 10/2017 |
| WO | 2017173206 A1 | 10/2017 |
| WO | 2017173256 A1 | 10/2017 |
| WO | 2017173384 A1 | 10/2017 |
| WO | 2017173410 A1 | 10/2017 |
| WO | 2018178238 A1 | 10/2018 |
| WO | 2018178240 A1 | 10/2018 |
| WO | 2018215315 A1 | 11/2018 |
| WO | 2018215316 A1 | 11/2018 |

OTHER PUBLICATIONS

Tomohiko Takasaki, What is Dengue Fever? (Dengunetsu to wa), National Institute Of Infectious Disease, Information of Infectious Diseases (Kansensyo Jouhou), 2014 (Wellknown art) (Japanese document).

Naziroglu et al., entitled "Synthesis and application of L-proline and R-phenylglycine derived organocatalysts for direct asymmetric Michael addition of cyclohexanone to nitroalkenes," Turk J Chem, 36 (2012), 659-670.

Aripo Office Action dated Feb. 10, 2016 in connection with African Patent Application No. AP/P/2014/007535.

Eurasian Office Action dated May 2016 in connection with Eurasian Patent Application No. 201490654, 1 page.

Summons to attend oral proceedings pursuant to Rule (115(1) EPC in connection with European Patent Application No. 12775463.8, Jul. 6, 2016.

New Zealand First Office Action dated Jul. 19, 2014 in connection with case No. 721700.

New Zealand Further Examination Report dated Jul. 19, 2016 in connection with case No. 622588.

Singapore Written Opinion dated Jul. 5, 2016 in connection with Singapore Patent Application No. Sep. 26, 2012.

Duan et al., entitled "Syntheses and Photochromic Studies of Dithienylethene-Containing Imidazolium Derivatives and Their Reactivity towards Nucleophiles," Chem. Eur. J. 2010, 16, 13199-13209.

STN International, RN 1316109-81-5, 1297049-96-7, 1297011-10-9, 1296377-78-0, 1295540-00-9, 1295460-37-5, 1294813-77-6, 1294288-37-1, 1293697-77-4, 1287503-18-7, 1287040-60-1, 1286579-37-0, 1277962-26-1, 1252467-88-1, 1181884-55-8, 1134766-19-0, 1118870-48-6, 1062132-16-4, 1030212-41-9, 1015662-06-2, 1014535-82-0, 1014493-63-0, 1012956-97-6, 1011162-23-4, 1011120-58-3, 1011119-79-1, 1011113-94-2, 931000-99-6, 920834-07-7, 878619-92-2, File Registry [online], Aug. 11, 2011, ED Mar. 30, 2006-Aug. 11, 2011.

Examination Report on Israeli Patent Application No. 231492, 3 pages, with Annex to Report, 1 page, Nov. 30, 2015.

Registry No. 1277962-26-1, entered in STN on Apr. 10, 2011.

Registry No. 924715-04-8, entered in STN on Mar. 4, 2007.

Registry No. 1386766-68-2, entered in STN on Aug. 6, 2012.

Registry No. 1388775-15-2, entered in STN on Aug. 9, 2012.

Registry No. 1388908-86-8, entered in STN on Aug. 14, 2012.

Registry No. 1386200-09-4, entered in STN on Aug. 3, 2012.

Registry No. 1388629-42-2, entered in STN on Aug. 9, 2012.

Japanese Office Action dated Jun. 2, 2020 from Japanese Patent Appln. No. JP2017-243354 (English language translation).

Registry No. 1219356-85-0 entered STN Apr. 15, 2010.

Registry No. 1041392-09-9 entered STN Aug. 17, 2008.

Registry No. 1036730-78-5 entered STN Jul. 28, 2008.

Japanese Office Action dated Apr. 21, 2016 in connection with Japanese Patent Application No. 2014-531279.

Prasad L. Polavarapu et al., "Intrinsic Rotation and Molecular Structure," Chirality 15: S143-S149 (2003).

Prevention of Dengue, Centers for Disease Control and Prevention, retrieved from the internet at https://www.cdc.gov/dengue/prevention/index.html, page last updated Sep. 27, 2012, retrieved from the intemet on Jan. 8, 2019, 2 pages.

Lidia Moreira Lima et al., "Bioisosterism: A Useful Strategy for Molecular Modification and Drug Design," Current Medicinal Chemistry, Bentham Science Publishers Ltd. (2005), vol. 12, pp. 23-49.

Ian Stansfield et al., "Development of carpoxylic acid replacements in indole-N-acetamide inhibitors of hepatitis C virus NS5B polymerase," Bioorganic & Medicinal Chemistry Letters, vol. 17 (2007) 5143-5149, ScienceDirect (2007), www.sciencedirect.com, internet.

Boltromeyuk V.V., Obshchaya khimiya (General Chemistry), Minsk, Vysheyshaya shkola, 2012, p. 65 (translation).

Wolff et al., Burger's Medicinal Chemistry and Drug Discovery, 5th Ed., vol. 1: Principles and Practice, pp. 975-977 (1995).

Banker et al., (1996) Modern Pharmaceuticals, 3rd Edition, Revised and Expanded, p. 596.

N.C.B.I.: "qHTS for inhibitors of binding or entry into cells for Marburg Virus," Pubchem Bioassay Record AID 540276, Jul. 2011, 13 pages, XP55641386, Retreved from the Internet: https://pubchem.ncbi.nlm.nih.gov/bioassay/540276.

EP Search Report dated Nov. 19, 2019 from European Patent Appln No. EP 19183201.3.

"Solvation," Wikipedia, at internet address: https://en.wikipedia.org/wiki/Solvation, web page last edited on Mar. 13, 2019, 6 pages.

Examination Report dated Jan. 7, 2020, from Indian Patent Appln. No. 201727014547.

ACS on STN Registry No. 931079-09-3, Apr. 20, 2007.

ACS on STN Registry No. 931007-71-5, Apr. 19, 2007.

ACS on STN Registry No. 930910-25-1, Apr. 19, 2007.

ACS on STN Registry No. 930724-99-5, Apr. 18, 2007.

ACS on STN Registry No. 930463-83-5, Apr. 17, 2007.

ACS on STN Registry No. 925399-60-6, Mar. 7, 2007.

(56) References Cited

OTHER PUBLICATIONS

ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007.
ACS on STN Registry No. 920827-69-6, Feb. 14, 2007.
ACS on STN Registry No. 920696-97-5, Feb. 13, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.
International Search Report and Written Opinion dated Aug. 22, 2016, for International Patent Application No. PCT/EP2016/059975.
Opposition filed in Ecuadorian Patent Application No. SENADI-2019-83621 (English language translation).
Opposition filed in Ecuadorian Patent Application No. SENADI-2019-83640 (English language translation).
ACS Registry No. 1295460-37-5, entered STN: May 16, 2011, “Registry Copyright 2015 ACS on STN,” p. 19.
ACS Registry 1252467-88-1, entered STN: Nov. 10, 2010, “Registry Copyright 2015 ACS on STN,” p. 20.
Database Pubchem [online] NCBI; Jul. 30, 2007, Pubchem CID: 16307180, 12 pages.
Database Pubchem [online] NCBI; Dec. 4, 2007, Pubchem CID: 18190680, 11 pages.
Database Pubchem [online] NCBI; Jul. 20, 2009, Pubchem CID: 42916879, 12 pages.
Database Pubchem [online] NCBI; Jul. 30, 2006, Pubchem CID: 8377731, 9 pages.
Database Pubchem [online] NCBI; Jul. 30, 2006, Pubchem CID: 8377750, 9 pages.
Database Pubchem [online] NCBI; Jul. 30, 2006, Pubchem CID: 8377765, 9 pages.
Database Pubchem [online] NCBI; Jul. 30, 2006, Pubchem CID: 8377782, 9 pages.
Database Pubchem [online] NCBI; Jul. 30, 2006, Pubchem CID: 8377825, 9 pages.
Database Pubchem [online] NCBI; Jul. 30, 2006, Pubchem CID: 8377845, 10 pages.
Database Pubchem [online] NCBI; Jul. 30, 2006, Pubchem CID: 8377864, 9 pages.
Database Pubchem [online] NCBI; Jul. 30, 2006, Pubchem CID: 8377894, 10 pages.
Database Pubchem [online] NCBI; Jul. 30, 2006, Pubchem CID: 8377913, 10 pages.
Database Pubchem [online] NCBI; Jul. 30, 2006, Pubchem CID: 8377936, 9 pages.
Database Pubchem [online] NCBI; Jul. 30, 2006, Pubchem CID: 8377950, 10 pages.
Database Pubchem [online] NCBI; Jul. 30, 2006, Pubchem CID: 8377957, 9 pages.
Database Pubchem [online] NCBI; Jul. 30, 2006, Pubchem CID: 8378071, 9 pages.
Database Pubchem [online] NCBI; Jul. 30, 2006, Pubchem CID: 8378972, 10 pages.
Database Pubchem [online] NCBI; Jul. 30, 2006, Pubchem CID: 9292530, 9 pages.
Database Pubchem [online] NCBI; Jul. 30, 2006, Pubchem CID: 9329202, 10 pages.
Database Pubchem [online] NCBI; Jul. 31, 2006, Pubchem CID: 9356704, 10 pages.
Database Pubchem [online] NCBI; Jul. 31, 2006, Pubchem CID: 9461840, 9 pages.
Database Pubchem [online] NCBI; Jul. 30, 2007, Pubchem CID: 16267760, 12 pages.
Database Pubchem [online] NCBI; Jul. 30, 2007, Pubchem CID: 16340406, 12 pages.
Database Pubchem [online] NCBI; Jul. 30, 2007, Pubchem CID: 16343459, 10 pages.
Database Pubchem [online] NCBI; Jul. 30, 2007, Pubchem CID: 16366089, 12 pages.
Database Pubchem [online] NCBI; Dec. 4, 2007, Pubchem CID: 18226977, 10 pages.
Database Pubchem [online] NCBI; Feb. 29, 2008, Pubchem CID: 24614828, 12 pages.
Database Pubchem [online] NCBI; Feb. 29, 2008, Pubchem CID: 24614964, 12 pages.
Database Pubchem [online] NCBI; Feb. 29, 2008, Pubchem CID: 24652310, 11 pages.
Database Pubchem [online] NCBI; May 28, 2009, Pubchem CID: 26654475, 9 pages.
Database Pubchem [online] NCBI; May 29, 2009, Pubchem CID: 31392427, 9 pages.
Database Pubchem [online] NCBI; May 30, 2009, Pubchem CID: 39912467, 9 pages.
Database Pubchem [online] NCBI; Nov. 25, 2010, Pubchem CID: 47065408, 12 pages.
Database Pubchem [online] NCBI; May 20, 2011, Pubchem CID: 52708600, 9 pages.
Database Pubchem [online] NCBI; May 20, 2011, Pubchem CID: 52764912, 9 pages.
Database Pubchem [online] NCBI; May 20, 2011, Pubchem CID: 52886897, 9 pages.
Database Pubchem [online] NCBI; Sep. 17, 2005, Database accession No. CID 4793342, 4 pages.
Database Pubchem [online] NCBI; Sep. 17, 2005, Database accession No. CID 4796066, 4 pages.
Database Pubchem [online] NCBI; Sep. 17, 2005, Database accession No. CID 4849237, 4 pages.
Database Pubchem [online] NCBI; Sep. 17, 2005, Database accession No. CID 4793878, 4 pages.
PubChem [online] 2006.07.30 PubChem CID 8377731, 12 pages.
The PCT International Search Report dated Nov. 29, 2012 in connection with PCT International Patent Application No. PCT/EP2012/69007, 4 pages.
Columbian Office Action dated Oct. 28, 2015 in connection with Colombian Patent Application No. 14-89597-8.
Declaration of Neil Thomas Simpkin Ba regarding certified English-language translation dated Jan. 19, 2015, 1 page.
Opposition in connection with patent family member, Costa Rican Patent Application No. 2014-0147 dated Nov. 14, 2014, 23 pages.
Invitation to Respond to Written Opinion dated Jan. 8, 2015, from the Intellectual Property Office of Singapore in connection with patent family member Singapore Application No. 11201400927W, 9 pages.
Li et al., entitled “Thiazolium-derived N-heterocyclic carbene-catalyzed cross-coupling of aldehydes with unactived imines,” Chem. Commun, 2007, 852-854.
Communication European Search Report dated Nov. 19, 2019, in connection with European Patent Application No. 19183201.3.
Bergman et al., Synthesis and reactions of some 3-(2-haloacyl)indoles. Tetrahedron 29: 971-976, 1973.
PCT Notification Concerning Transmittal of International Preliminary Report on Patentability and Written Opinion of the International Searching Authority dated Apr. 10, 2014 in connection with PCT International Patent Application No. PCT/EP2012/069007, 9 pages.
Office Action dated Jun. 4, 2015 in connection with Columbian Patent Application No. 14-89597-5, 26 pages.
Registry No. 1241127-58-1, entered in STN on Sep. 15, 2010.
Registry No. 1062257-51-5, entered in STN on Oct. 16, 2008.
Registry No. 1062132-16-4, entered in STN on Oct. 16, 2008.
Registry No. 1030735-63-7, entered in STN on Jun. 26, 2008.
Registry No. 1030232-46-2, entered in STN on Jun. 24, 2008.
Registry No. 1014493-63-0, entered in STN on Apr. 14, 2008.
Database Pubchem [online] NCBI; Jul. 31, 2006, Pubchem CID: 9356705, 3 page.
Database Pubchem [online] NCBI; May 29, 2009, Pubchem CID: 31392243, 1 page.

(56) References Cited

OTHER PUBLICATIONS

Database Pubchem [online] NCBI; May 29, 2009, Pubcchem CID: 37329396, 2 pages.
Office Action dated Jun. 25, 2018 that issued in connection with patent family member Peruvian Patent Application.
English translation of an Office Action dated May 4, 2018 that issued in connection with patent family member Eurasian Patent Application No. 201490654.
English translation of an Office Action dated Jun. 22, 2018 issued in connection with patent family member Uzbekistan Patent Application.
English translation of an Office Action dated Jun. 28, 2018 that issued in connection with patent family member Chilean Divisional Patent Application No. 201601580.
Canadian Office Action dated May 2, 2018 that issued in connection with patent family member Canadian Patent App. No. 2,848,604.
New Zealand Further Examination Report dated Jan. 19, 2018 in connection with New Zealand Patent Application No. 721700.
Wei-Kung Wang et al., High Levels of plasma Dengue Viral Load during Defervescence in Patients with Dengue Hemorrhagic Fever: Implications for Pathogenesis, Virology, 2003, 305, 330-338.
Rotem Ben-Shachar et al., Drivers of Inter-individual Variation in Dengue Viral Load Dynamics, PLoS Computational Biology, 2016, 12 (11), e1005194.

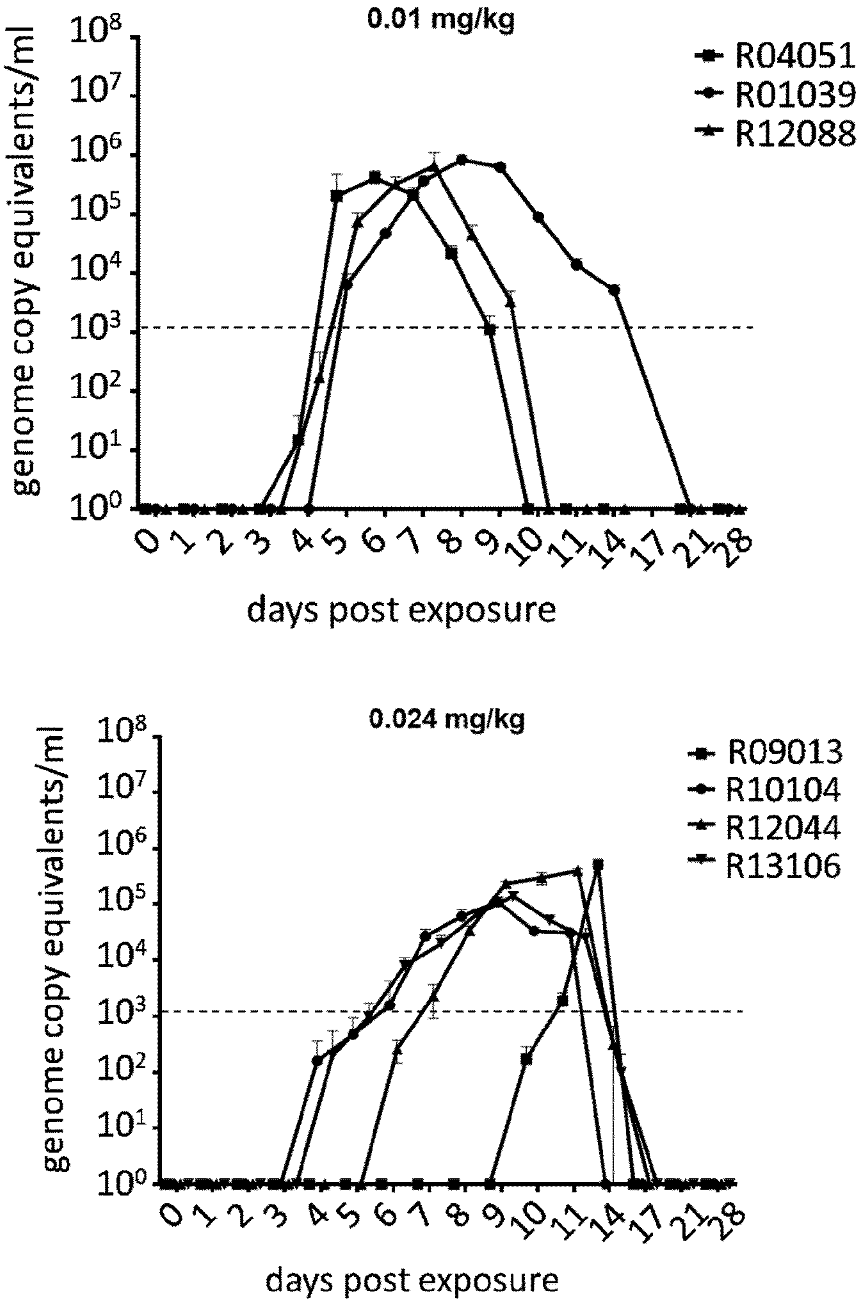
FIGURE 12A (Continuation)

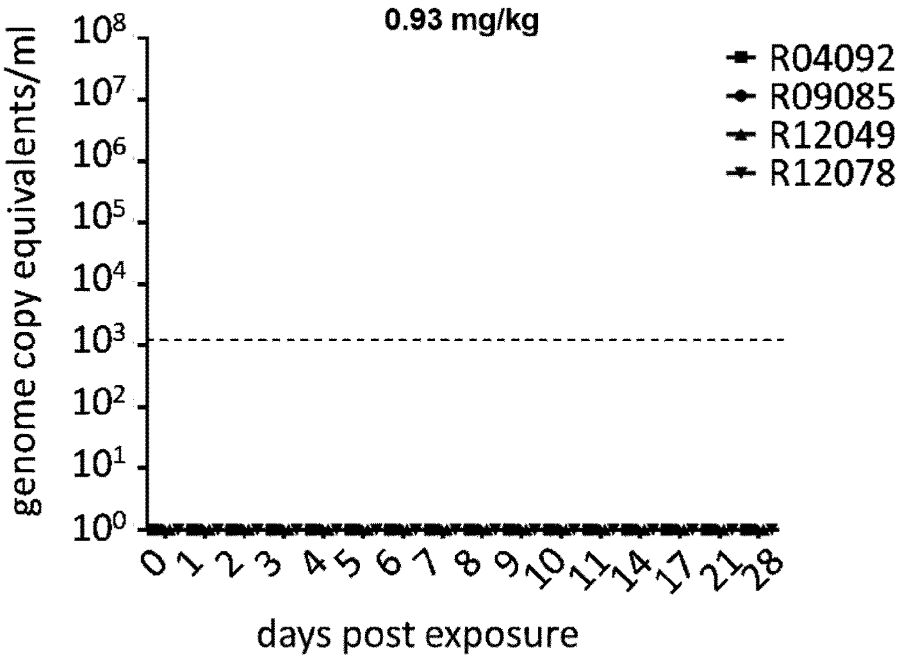
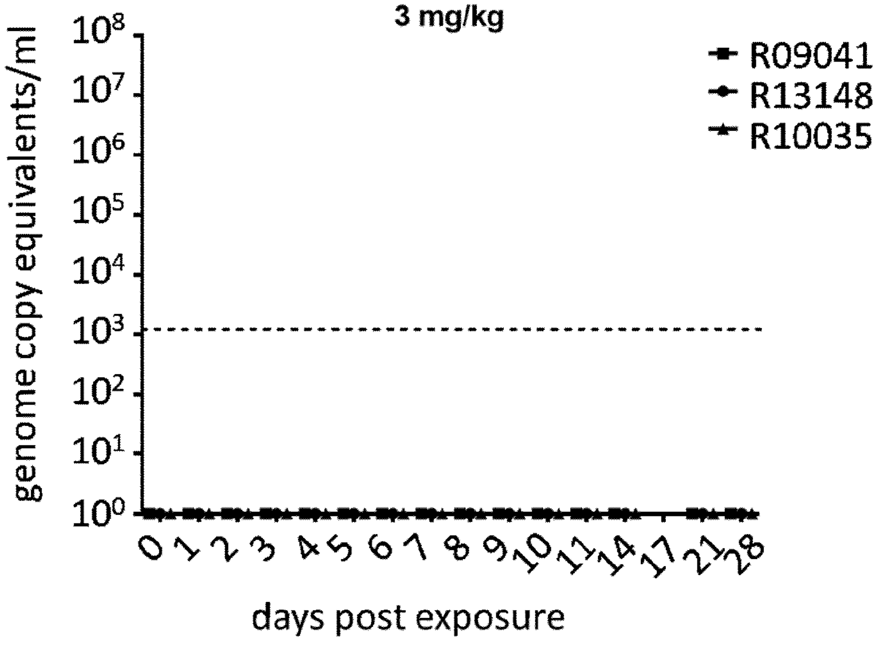
FIGURE 12B (Continuation)

TREATMENT AND PREVENTION OF DENGUE DISEASE

RELATED APPLICATIONS

This application is a 35 U.S.C. § 371 nationalization of PCT application PCT/EP2020/082102 filed Nov. 13, 2020, which claims priority to European Patent Application 19209593.3 filed Nov. 15, 2019, European Patent Application 19213851.9 filed Dec. 5, 2019, and European Patent Application 20171172.8 filed Apr. 23, 2020, each of which is incorporated by reference herein for all purposes.

The present invention relates to the use of substituted indole derivatives and substituted indoline derivatives in the manufacture of a medicament for the treatment or the prevention of dengue disease in an individual at risk of being infected by Dengue virus. The invention further provides a method for the treatment or the prevention of dengue disease in an individual at risk of being infected by Dengue virus.

BACKGROUND OF THE INVENTION

Dengue is caused by any of the 4 antigenically distinct DENV serotypes (DENV-1, -2, -3, and -4), which belong to the genus Flavivirus in the family of the Flaviviridae. The DENVs are human pathogens which are transmitted through the bite of an infected female mosquito of the genus *Aedes*, mainly of the species *Aedes aegypti* and to a lesser extent *Aedes albopictus* (Carrington et al., 2014). Dengue is endemic in more than 125 countries, and has also again become endemic in the United States (US) territories of Puerto Rico, American Samoa, and the Virgin Islands (CDC, 2019). About half of the global population is currently at risk of becoming infected with DENV (Bhatt et al., 2013; Brady et al., 2012; WHO, 2019). According to the World Health Organization (WHO), dengue is among the top 10 threats to global health in 2019 (WHO, 2019).

The actual numbers of dengue cases are underreported. It is estimated that there are 390 million DENV infections globally per year, of which 96 million manifests clinically (with any severity of the disease) (Bhatt et al., 2013). On average, each year about 500,000 dengue cases require hospitalization due to severe and life-threatening disease and up to 25,000 patients die due to dengue.

During a primary DENV infection, 75% of the individuals remain asymptomatic. Those that show clinical symptoms mainly develop an acute, self-limiting febrile illness. The first clinical symptoms occur 3 to 8 days after a bite by a DENV-infected and viremic mosquito. Resolution of infection usually occurs within 4 to 7 days due to a robust innate and adaptive immune response (Whitehorn and Simmons., 2011). A smaller percentage of DENV infections result in severe dengue outcomes such as dengue hemorrhagic fever and dengue shock syndrome. Secondary DENV infections or infections with particularly virulent viral strains are thought to be associated with an increased risk for severe dengue (Murray et al., 2013).

During classical dengue fever, an abrupt onset of fever is accompanied by a wide range of potential symptoms, i.e., myalgia, arthralgia, headache, and rash; with retro-orbital pain and lower back pain being prototypical symptoms. Also vomiting, nausea, and anorexia are common (WHO, 2009). During this febrile phase, severe and non-severe dengue cases cannot be distinguished. The critical phase is characterized by an increased propensity for capillary leakage and hemorrhage, typically manifested by scattered petechiae, hematuria, and gastrointestinal hemorrhage (Whitehorn and Simmons, 2011; Murray et al., 2013). Without early diagnosis and proper management, some patients experience shock from blood loss or plasma leakage, which can result in a sudden deterioration of the patient's condition (Gubler, 1998).

Currently, there is no dengue-specific treatment available and thus, clinical treatment is principally supportive in nature.

In December 2015, the first vaccine against DENV was licensed in Mexico. The chimeric yellow fever—DENV tetravalent dengue vaccine (CYD-TDV; Dengvaxia®) is a tetravalent live attenuated vaccine developed by Sanofi Pasteur. By November 2016, the vaccine had been approved for use in 18 countries including Brazil, Mexico, El Salvador, Costa Rica, and the Philippines. Recently, the vaccine was also approved in the US for the prevention of dengue disease caused by all DENV serotypes (DENV-1, DENV-2, DENV-3, and DENV-4) in people, 9 to 16 years of age, who have laboratory-confirmed previous dengue infection and who live in endemic areas. The widespread use of the vaccine, however, is not foreseen per the WHO working group for immunization, as a number of factors need further consideration (WHO, 2017). The Strategic Advisory Group of Experts recommended countries to consider the introduction of Dengvaxia® only in geographic settings (national or subnational) with high dengue endemicity.

During recent years, drugs developed for prophylactic use are slowly getting more attention as potential alternatives to prevent dengue (Whitehorn et al., 2014). Prophylaxis could be beneficial for travelers to dengue-endemic regions (e.g., aid workers, tourists, business and military travelers, and expatriates), as well as for vulnerable populations living in endemic regions. By preventing viremia and/or by reducing viral load, dengue-associated morbidity and mortality could be reduced remarkably or even prevented (Whitehorn et al., 2014). In addition, an efficacious and safe dengue antiviral compound could still have its use as a therapeutic agent as well.

WO 2017/167951 and WO 2016/180696 disclose compounds for the prevention and treatment of dengue viral infections. There is, however, a great unmet medical need for medicaments allowing the treatment or the prevention of dengue disease (also called dengue) in animals, more in particular in humans.

The present invention relates to the use of substituted indole derivatives and substituted indoline derivatives in the manufacture of a medicament for the treatment of dengue disease in an individual infected with Dengue virus or the prevention of dengue disease in an individual at risk of being infected by Dengue virus. The invention further provides a method for the treatment of dengue disease in an individual infected with Dengue virus or the prevention of dengue disease in an individual at risk of being infected by Dengue virus.

SUMMARY OF THE INVENTION

In a first aspect, the present invention provides for the use of substituted indole derivatives and/or substituted indoline derivatives in the manufacture of a medicament for the prevention of dengue in an individual at risk of being infected by Dengue virus. The medicament is preferably administered intermittently at a time interval of at least 6 hours, preferably at least 12 hours, preferably at least 20 hours, more preferably at least 24 hours, more preferably at least 36 hours, more preferably at least 48 hours, more preferably at least 72 hours. The substituted indole derivatives and/or substituted indoline derivatives are as described herein. The invention further provides for the use of substituted indole derivatives and/or substituted indoline derivatives in the manufacture of a medicament for the treatment of dengue disease in an individual infected by Dengue virus.

In a second aspect, the present invention provides a method for the prevention of dengue in an individual at risk of being infected by Dengue virus. Said method comprises administering to the individual at risk a medicament comprising substituted indole derivatives and/or substituted indoline derivatives wherein the medicament is administered intermittently at a time interval of at least 6 hours, preferably at least 12 hours, preferably at least 20 hours, more preferably at least 24 hours, more preferably at least 36 hours, more preferably at least 48 hours, more preferably at least 72 hours. The substituted indole derivatives and/or substituted indoline derivatives are as described below. The invention further provides a method for the treatment of dengue in an individual infected by Dengue virus.

The present invention provides for the use of compounds for the prevention, also called prophylactic treatment or pre-exposure prophylaxis, of dengue disease. The concept behind prophylaxis is that the compound would be present and displays a sufficient level of systemic exposure prior to viral infection and/or prior to the time point that the viremia reaches its peak (peak viral load). The invention leads to a considerable inhibition of dengue viral replication, thereby minimizing and even eliminating the risk of contracting dengue. This is beneficial for multiple populations including but not limited to populations living in endemic regions and travelers to dengue endemic regions such as aid workers, tourists, business and military travelers, and those visiting friends and family.

DETAILED DESCRIPTION OF THE INVENTION

Figure 1:
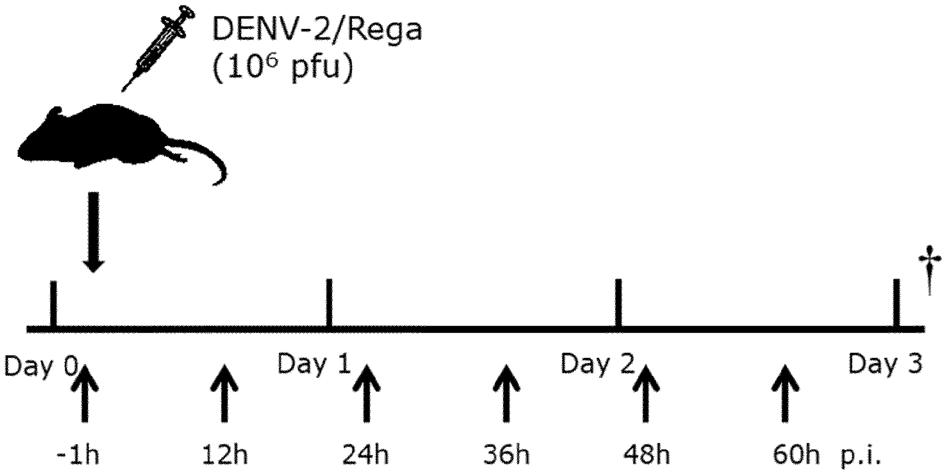
FIG. 1: Schematic representation of the in vivo viremia AG129 mouse experiment where compound (a) is tested for efficacy against a high viral input or inoculum of DENV-2/Rega of $10^6$ plaque forming unit (PFU). The arrows at the bottom of the figure indicate administration of compound (a)/vehicle. At day 0, 1 hour after the first administration of compound (a), the mice were infected intraperitoneal (i.p.) with $10^6$ PFU DENV-2/Rega.

The present invention provides for the prevention, also called prophylactic treatment, of dengue disease. The terms prophylactic and prophylaxis as used herein, refer to Post-Exposure Prophylaxis (PEP), and Pre-Exposure Prophylaxis (PrEP). PEP, also known as post-exposure prevention, refers to treatment initiated after exposure to the Dengue virus and preferably before reaching peak viral load. PrEP refers to treatment initiated before exposure to the Dengue virus. The invention further relates to the treatment of dengue disease. Treatment is used herein to refer to treatment initiated after exposure to the Dengue virus and preferably after reaching peak viral load and/or symptoms manifestations.

In a first aspect, the present invention provides for the use of a compound of formula I or formula II in the manufacture of a medicament for the prevention of dengue infection or disease in an individual at risk of being infected by Dengue virus, wherein the medicament is administered intermittently at a time interval of at least 6 hours, preferably at least 12 hours, preferably at least 20 hours, preferably at least 24 hours and wherein compound of formula I corresponds to

I

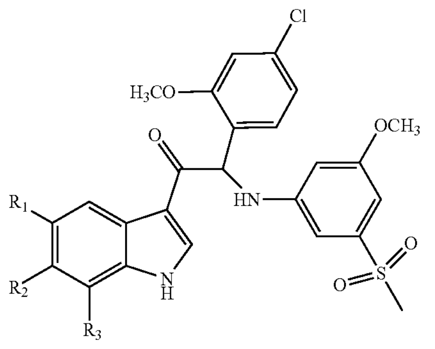

a stereo-isomeric form, a pharmaceutically acceptable salt, solvate or polymorph thereof; said compound is selected from the group wherein:

$R_1$ is H, $R_2$ is F and $R_3$ is H or $CH_3$, $R_1$ is H, $CH_3$ or F, $R_2$ is $OCH_3$ and $R_3$ is H, $R_1$ is H, $R_2$ is $OCH_3$ and $R_3$ is $CH_3$, $R_1$ is $CH_3$, $R_2$ is F and $R_3$ is H, $R_1$ is $CF_3$ or $OCF_3$, $R_2$ is H and $R_3$ is H, $R_1$ is $OCF_3$, $R_2$ is $OCH_3$ and $R_3$ is H, $R_1$ is $OCF_3$, $R_2$ is H and $R_3$ is $CH_3$, and compound of formula II corresponds to

II

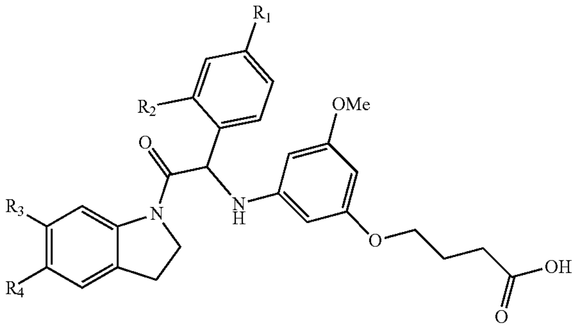

a stereoisomeric form, a pharmaceutically acceptable salt, solvate or polymorph thereof, wherein $R_1$ is chloro, $R_2$ is hydrogen, $R_3$ is trifluoromethyl, and $R_4$ is hydrogen; or $R_1$ is chloro, $R_2$ is hydrogen, $R_3$ is trifluoromethoxy, and $R_4$ is hydrogen; or $R_1$ is chloro, $R_2$ is hydrogen, $R_3$ is trifluoromethyl, and $R_4$ is methoxy; or $R_1$ is chloro, $R_2$ is methoxy, $R_3$ is trifluoromethyl, and $R_4$ is hydrogen; or $R_1$ is chloro, $R_2$ is methoxy, $R_3$ is trifluoromethyl, and $R_4$ is methoxy; or $R_1$ is chloro, $R_2$ is methoxy, $R_3$ is trifluoromethoxy, and $R_4$ is hydrogen; or $R_1$ is chloro, $R_2$ is fluoro, $R_3$ is trifluoromethyl, and $R_4$ is hydrogen; or $R_1$ is chloro, $R_2$ is fluoro, $R_3$ is trifluoromethoxy, and $R_4$ is hydrogen; or $R_1$ is chloro, $R_2$ is fluoro, $R_3$ is trifluoromethyl, and $R_4$ is methoxy; or $R_1$ is chloro, $R_2$ is hydrogen, $R_3$ is trifluoromethoxy, and $R_4$ is methoxy.

The present invention also provides a compound of formula I for use in the prevention of dengue disease in an individual at risk of being infected by Dengue virus or for the treatment of dengue disease in an individual infected by Dengue virus wherein the compound is comprised in a medicament which is administered intermittently at a time interval of at least 6 hours, preferably at least 12 hours, preferably at least 20 hours, preferably at least 24 hours, preferably at least 36 hours, preferably at least 48 hours, preferably at least 72 hours, and wherein formula I corresponds to

I

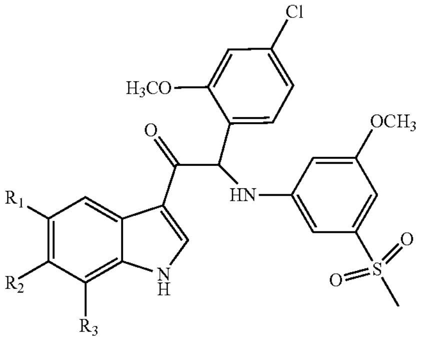

a stereo-isomeric form, a pharmaceutically acceptable salt, solvate or polymorph thereof; said compound is selected from the group wherein:

$R_1$ is H, $R_2$ is F and $R_3$ is H or $CH_3$, $R_1$ is H, $CH_3$ or F, $R_2$ is $OCH_3$ and $R_3$ is H, $R_1$ is H, $R_2$ is $OCH_3$ and $R_3$ is $CH_3$, $R_1$ is $CH_3$, $R_2$ is F and $R_3$ is H, $R_1$ is $CF_3$ or $OCF_3$, $R_2$ is H and $R_3$ is H, $R_1$ is $OCF_3$, $R_2$ is $OCH_3$ and $R_3$ is H, $R_1$ is $OCF_3$, $R_2$ is H and $R_3$ is $CH_3$.

Included within the scope of the present invention are all stereo-isomeric forms of the compounds of formula I or formula II, including mixtures of one or more thereof.

Included within the scope of the present invention are anhydrous forms of the compounds of formula I or formula II.

Included within the scope of the present invention are amorphous forms of the compounds of formula I or formula II.

Preferably compound of formula I or its stereo-isomeric form, a pharmaceutically acceptable salt, solvate or polymorph thereof is selected from the group:

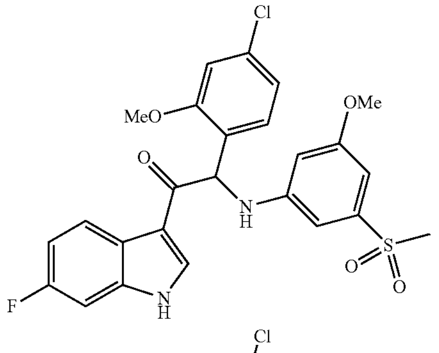

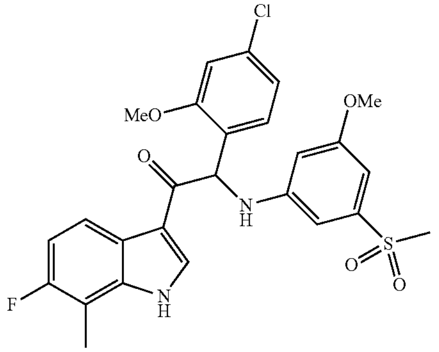

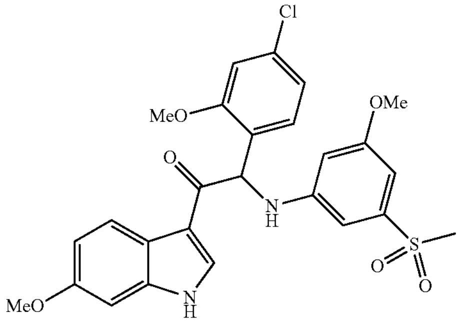

-continued
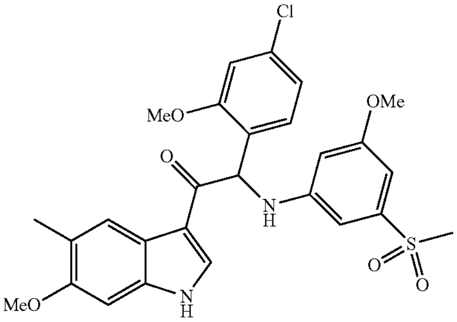
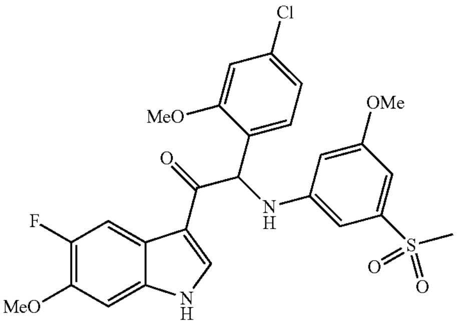
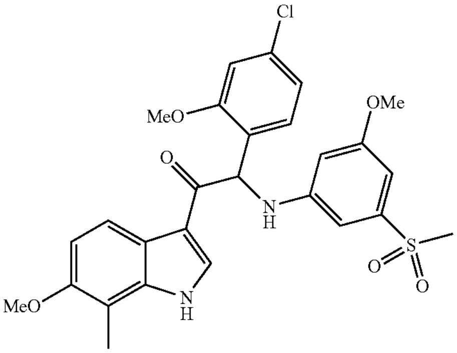
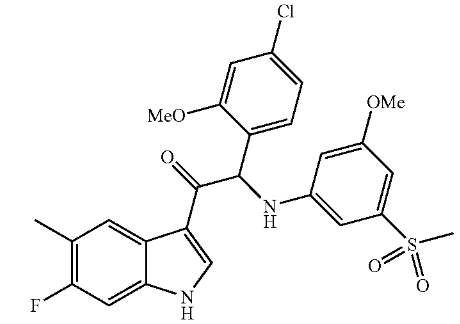
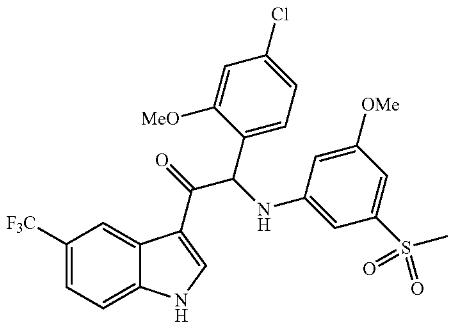
-continued
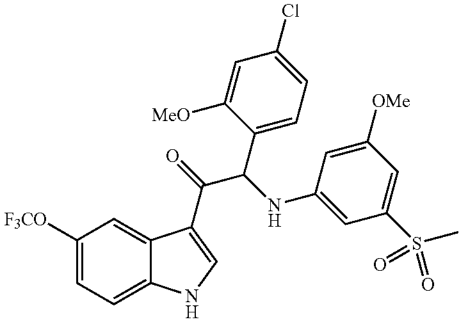
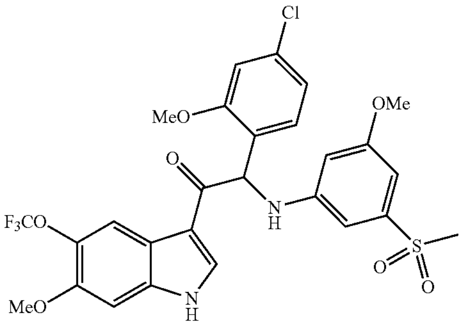
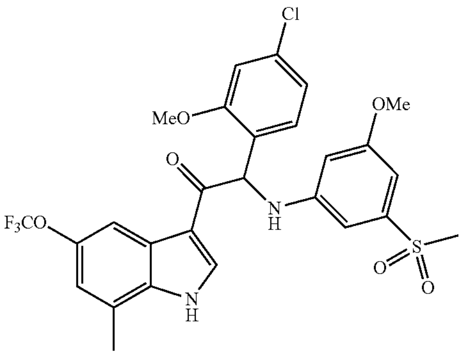
Preferably compound of formula II or its stereo-isomeric form, a pharmaceutically acceptable salt, solvate or polymorph thereof is selected from the group:
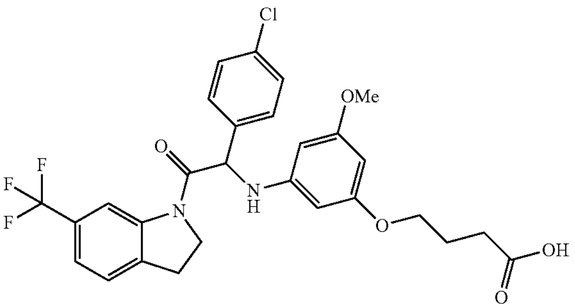

-continued

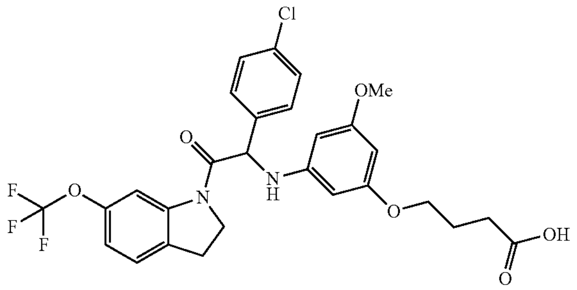

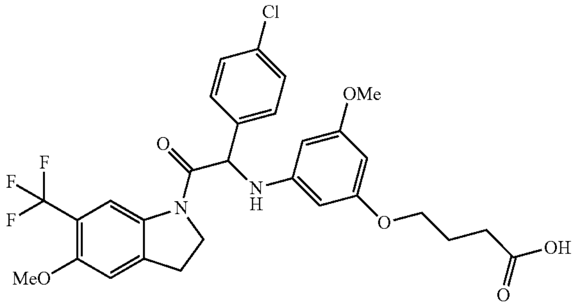

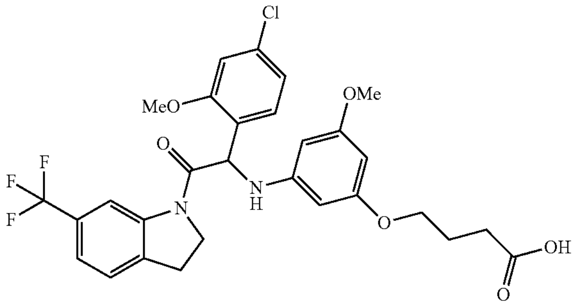

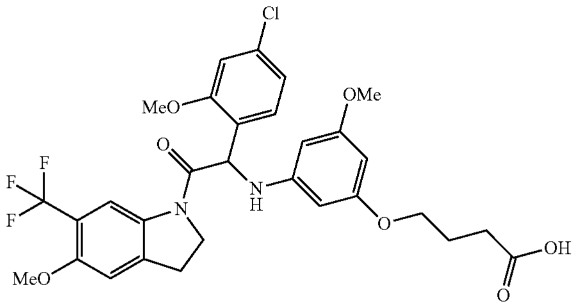

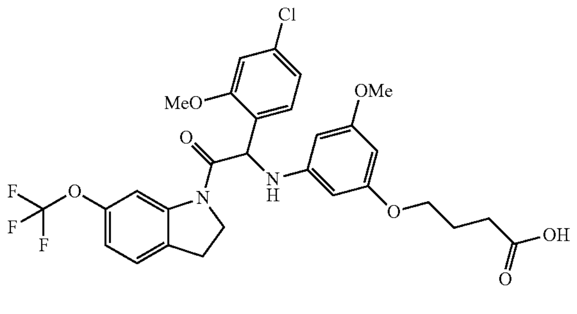

-continued

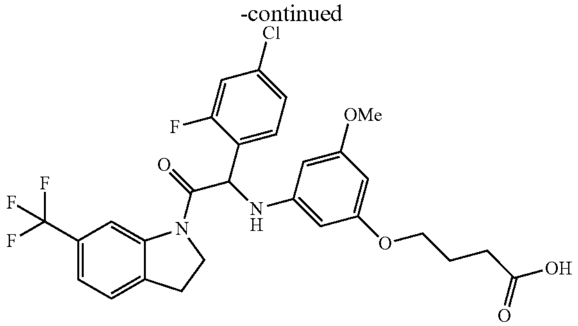

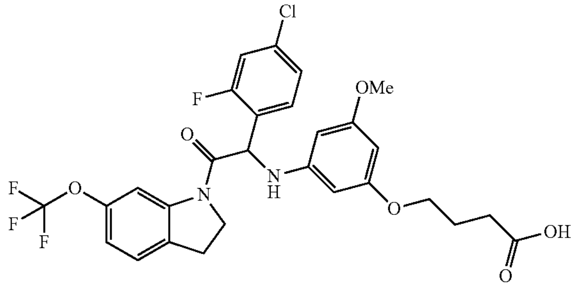

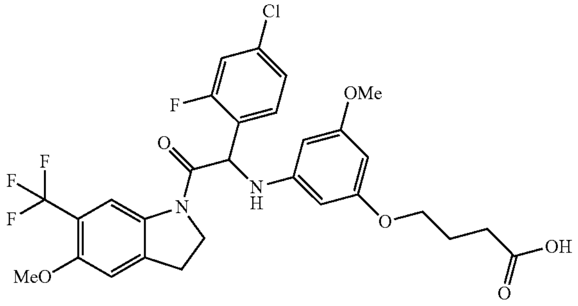

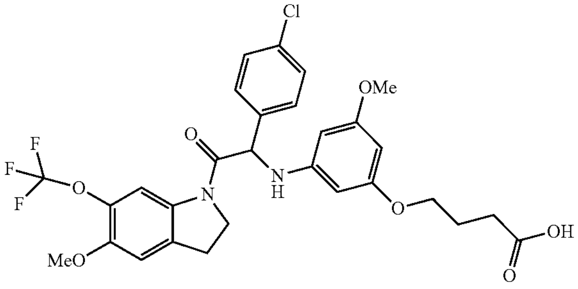

Pharmaceutically acceptable salts of the compounds of formula I and II include the acid addition and base salts thereof. Suitable acid addition salts are formed from acids which form non-toxic salts. Suitable base salts are formed from bases which form non-toxic salts.

The compounds of formula I and II may be used in un-solvated and solvated forms. The term “solvate” is used herein to describe a molecular complex comprising the compound of formula I and II and one or more pharmaceutically acceptable solvent molecules, for example, ethanol.

The compounds of formula I according to the present invention may be synthesized according to methods described in the art, as disclosed in WO 2016/180696. The compounds of formula II according to the present invention may be prepared according to methods described in the art, as disclosed in WO2017/167951.

In a preferred embodiment, the compound of Formula (I) is compound (a)

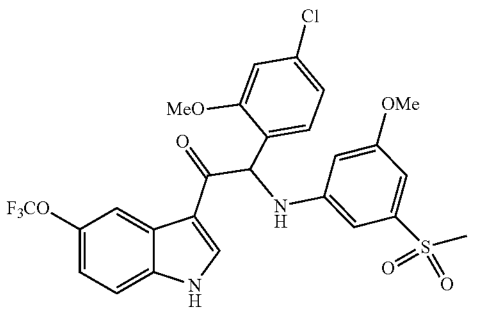

or a stereo-isomeric form, a pharmaceutically acceptable salt, solvate or polymorph thereof. Compound (a) may be in a solvated form, for example as a monohydrate.

Preferably the compound of Formula (I) is the (S)-enantiomer of Compound (a). Preferably compound (a) is in anhydrous form. Preferably, compound (a) is in amorphous form.

Preferably compound (a) or a pharmaceutically acceptable salt form thereof is in amorphous form or dissolved state. Preferably, compound (a) is in amorphous form or dissolved state. Preferably, the compound of Formula (I) is the (S)-enantiomer in amorphous form. Preferably, the compound of Formula (I) is the (S)-enantiomer in anhydrous form. Preferably, compound (a) is the (S)-enantiomer in amorphous form. Preferably, the compound (a) is the (S)-enantiomer in anhydrous form.

The compounds may be administered as crystalline or amorphous products. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The term "polymorph" refers to the ability of the compounds of formula I and II to exist in more than one form or crystal structure.

Preferably, the medicament is administered at least once every 6 hours, at least once every 8 hours, at least once every 12 hours, at least once every 20 hours at least once every 24 hours, at least once every 36 hours, at least once every 48 hours, at least once every 72 hours, at least once every week, at least once every two weeks, at least once every three weeks, at least once every month, at least once every 6 weeks, at least once every two months, at least once every three months, at least once every four months, at least once every five months, at least once every sixth months or at least once a year. The term "month" and "4 weeks" are used herein as equivalents.

The medicament may be administered to an individual at risk of being infected by Dengue virus. Said individual is living in or traveling to a dengue endemic region. The medicament may be also administered to an individual who is already infected by Dengue virus but the peak viral load in blood has not yet been reached. Preferably, for individuals at risk of being infected by Dengue virus, the first administration of the medicament is occurring at least 5 minutes, at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 24 hours, at least 36 hours, at least 48 hours, at least 72 hours, at least one week, at least two weeks, at least three weeks, at least one month, at least two months, at least three months, at least four months prior to infection (so for example prior to entering into an endemic geographical area for travelers or prior to dengue season for individuals living in endemic regions). The first administration of the medicament may also occur at most 15 days, at most 14 days, at most 13 days, at most 12 days, at most 11 days, at most 10 days, at most 8 days, at most 6 days, at most 5 days, at most 4 days, at most 72 hours, at most 48 hours, at most 36 hours, at most 24 hours or at most 12 hours after being infected by Dengue virus.

The medicament comprises an effective amount of compound of formula I or formula II. Said effective amount is selected such that dengue viral load in blood is kept during a prolonged period of time at a level of at most 0 copies/mL, at most 0.5 $log_{10}$ copies/mL, at most 1 $log_{10}$ copies/mL, at most 1.5 $log_{10}$ copies/mL, at most 2 $log_{10}$ copies/mL, at most 2.5 $log_{10}$ copies/mL, at most 3 $log_{10}$ copies/mL, at most 3.5 $log_{10}$ copies/mL, at most 4 $log_{10}$ copies/mL, at most 4.5 $log_{10}$ copies/mL, at most 5 $log_{10}$ copies/mL, at most 5.5 $log_{10}$ copies/mL, at most 6 $log_{10}$ copies/mL, at most 6.5 $log_{10}$ copies/mL, at most 7 $log_{10}$ copies/mL, at most 7.5 $log_{10}$ copies/mL, at most 8 $log_{10}$ copies/mL, at most 8.5 $log_{10}$ copies/mL, at most 9 $log_{10}$ copies/mL, at most 9.5 $log_{10}$ copies/mL, at most 10 $log_{10}$ copies/mL, at most 10.5 $log_{10}$ copies/mL, at most 11 $log_{10}$ copies/mL, at most 11.5 $log_{10}$ copies/mL, at most 12 $log_{10}$ copies/mL, at most 12.5 $log_{10}$ copies/mL, at most 13 $log_{10}$ copies/mL, at most 13.5 $log_{10}$ copies/mL, at most 14 $log_{10}$ copies/mL, at most 15 $log_{10}$ copies/mL.

Said effective amount is selected such that dengue viral load in blood is kept at a level of at most 0 copies/mL, at most 0.5 $log_{10}$ copies/mL, at most 1 $log_{10}$ copies/mL, at most 1.5 $log_{10}$ copies/mL, at most 2 $log_{10}$ copies/mL, at most 2.5 $log_{10}$ copies/mL, at most 3 $log_{10}$ copies/mL, at most 3.5 $log_{10}$ copies/mL, at most 4 $log_{10}$ copies/mL, at most 4.5 $log_{10}$ copies/mL, at most 5 $log_{10}$ copies/mL, at most 5.5 $log_{10}$ copies/mL, at most 6 $log_{10}$ copies/mL, at most 6.5 $log_{10}$ copies/mL, at most 7 $log_{10}$ copies/mL, at most 7.5 $log_{10}$ copies/mL, at most 8 $log_{10}$ copies/mL, at most 8.5 $log_{10}$ copies/mL, at most 9 $log_{10}$ copies/mL, at most 9.5 $log_{10}$ copies/mL, at most 10 $log_{10}$ copies/mL, at most 10.5 $log_{10}$ copies/mL, at most 11 $log_{10}$ copies/mL, at most 11.5 $log_{10}$ copies/mL, at most 12 $log_{10}$ copies/mL, at most 12.5 $log_{10}$ copies/mL, at most 13 $log_{10}$ copies/mL, at most 13.5 $log_{10}$ copies/mL, at most 14 $log_{10}$ copies/mL, at most 15 $log_{10}$ copies/mL.

Preferably, the effective amount of compound of formula I or formula II is selected such that dengue viral load in blood is kept during a prolonged period of time at a level of at most 2 $log_{10}$ copies/mL, at most 2.5 $log_{10}$ copies/mL, at most 3 $log_{10}$ copies/mL, at most 3.5 $log_{10}$ copies/mL, at most 4 $log_{10}$ copies/mL, at most 4.5 $log_{10}$ copies/mL, at most 5 $log_{10}$ copies/mL, at most 5.5 $log_{10}$ copies/mL, at most 6 $log_{10}$ copies/mL, at most 6.5 $log_{10}$ copies/mL, at most 7 $log_{10}$ copies/mL, at most 7.5 $log_{10}$ copies/mL, at most 8 $log_{10}$ copies/mL, at most 8.5 $log_{10}$ copies/mL, at most 9 $log_{10}$ copies/mL.

Preferably, the effective amount of compound of formula I or formula II is selected such that dengue viral load in blood is kept at a level of at most 2 $log_{10}$ copies/mL, at most 2.5 $\log_{10}$ copies/mL, at most 3 $\log_{10}$ copies/mL, at most 3.5 $\log_{10}$ copies/mL, at most 4 $\log_{10}$ copies/mL, at most 4.5 $\log_{10}$ copies/mL, at most 5 $\log_{10}$ copies/mL, at most 5.5 $\log_{10}$ copies/mL, at most 6 $\log_{10}$ copies/mL, at most 6.5 $\log_{10}$ copies/mL, at most 7 $\log_{10}$ copies/mL, at most 7.5 $\log_{10}$ copies/mL, at most 8 $\log_{10}$ copies/mL, at most 8.5 $\log_{10}$ copies/mL, at most 9 $\log_{10}$ copies/mL.

Prolonged period of time refers to a period of at least 6 hours, at least 12 hours, at least 24 hours, at least 36 hours, at least 48 hours, at least 72 hours, at least 1 week, at least 2 weeks, at least 3 weeks or at least 4 weeks. Said prolonged period of time refers to a period of at most 1 year, at most 6 months, at most 5 months, at most 4 months, at most 3 months or at most 2 months.

Preferably, the medicament is administered orally, subcutaneously, intramuscularly, or intravenously.

The medicament may be formulated into various pharmaceutical forms for different administration purposes. The medicament comprises an effective amount of any compound mentioned above or a mixture thereof, optionally in addition salt form, as the active ingredient. Said active ingredient may be combined in intimate admixture with a pharmaceutically acceptable carrier, which carrier may take a wide variety of forms depending on the form of preparation desired for administration. The medicament may be in unitary dosage form suitable, for example, for oral, topical, rectal or any other administration route known to the person skilled in the art. For example, in preparing the medicament as oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. The medicament may also be in solid form preparations that can be converted, shortly before use, to liquid forms.

It is especially advantageous to formulate the aforementioned medicament in unit dosage form for ease of administration and/or uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The effective amount of compound of formula I or formula II comprised in the medicament (for example a single tablet or dosage form) is of from 0.05 mg/kg to 500 mg/kg body weight, from 0.1 mg/kg to 400 mg/kg body weight, from 0.5 mg/kg to 300 mg/kg body weight, from 1 mg/kg to 200 mg/kg body weight, from 1.5 to 180 mg/kg body weight, from 3 mg/kg to 150 mg/kg body weight, from 5 mg/kg to 120 mg/kg body weight, from 6 mg/kg to 110 mg/kg body weight, from 10 mg/kg to 100 mg/kg body weight, from 15 mg/kg to 90 mg/kg body weight, from 20 mg/kg to 80 mg/kg body weight, from 25 mg/kg to 70 mg/kg body weight, from 30 mg/kg to 60 mg/kg body weight, from 35 mg/kg to 55 mg/kg body weight, from 40 mg/kg to 50 mg/kg body weight, from 42 to 45 mg/kg body weight or around 43 mg/kg body weight.

The effective daily amount of compound of formula I or formula II is of from 0.1 to 2400 mg, from 0.2 to 2000 mg, from 0.3 mg to 1600 mg, 0.5 mg to 1500 mg, from 1 mg to 1400 mg, from 2 mg to 1300 mg, from 3 mg to 1200 mg, from 4 mg to 1100 mg, from 5 mg to 1000 mg, from 6 mg to 950 mg, from 7 mg to 900 mg, from 8 mg to 850 mg, from 9 mg to 800 mg, from 10 mg to 750 mg, from 11 mg to 700 mg, from 12 mg to 650 mg, from 13 mg to 600 mg, from 14 mg to 550 mg, from 15 mg to 500 mg, from 16 mg to 450 mg, from 17 mg to 400 mg, from 18 mg to 350 mg, from 19 mg to 300 mg, from 20 mg to 250 mg, from 21 mg to 200 mg, from 22 mg to 150 mg, from 23 mg to 100 mg, from 24 mg to 95 mg, from 25 mg to 90 mg, from 26 mg to 85 mg, from 27 mg to 80 mg, from 28 mg to 75 mg, from 29 mg to 70 mg, from 30 mg to 65 mg, from 31 mg to 60 mg, from 32 mg to 55 mg, from 33 mg to 50 mg, from 34 mg to 45 mg, from 35 mg to 40 mg, from 36 mg to 38 mg. Effective daily amount refers herein to the amount of compound of formula I or formula II to be administered per day or per 24 hours.

The effective daily amount of compound may remain unchanged during the prophylaxis treatment period. Said effective daily dose or amount may also be variable such that it may decrease and/or increase during the indicated prophylaxis treatment period. Said effective daily amount may be reached by administration of medicaments which comprise unchanged or different concentrations (or effective amount) of compound of the invention.

Compounds of formula I or II as described herein may also be used in the manufacture of a medicament for the treatment of dengue disease. The medicament is preferably administered 1, 2, 3 or 4 times per day.

All previous embodiments, described above, are also applicable to the medicament comprising compounds of formula I or II and used for the treatment of dengue infections; Said embodiments include:

- The effective amount of compound of formula I or formula II comprised in the medicament is selected such that dengue viral load in blood is kept as described above,
- the medicament administration and formulation,
- The effective amount of compound of formula I or formula II comprised in the medicament (for example a single tablet or dosage form), and
- The effective daily amount of compound of formula I or formula II.

The effective daily amount of compound may remain unchanged during the treatment period.

Said effective daily dose or amount may also be variable such that it may decrease and/or increase during the indicated treatment period. Said effective daily amount may be reached by administration of medicaments which comprise unchanged or different concentrations of compound of the invention.

In a second aspect, the present invention provides a method for the treatment of dengue disease in an individual infected by Dengue virus or the prevention of dengue disease in an individual at risk of being infected by Dengue virus, said method comprising the step of administering to said individual a medicament comprising compound of formula I or formula II, wherein the medicament is administered intermittently at a time interval of at least 6 hours, preferably at least 12 hours, preferably at least 20 hours, more preferably at least 24 hours, more preferably at least 36 hours, more preferably at least 48 hours, more preferably at least 72 hours, and wherein the compounds of formula I and formula II are as described above in the first aspect of the invention.

In a preferred embodiment of the method, the medicament is administered as specified above in the first aspect of the invention including the administration timing of the medicament. In a preferred embodiment of the method, the medicament comprises an effective amount of compound of formula I or formula II, said effective amount is selected and has a value as specified above in the first aspect of the invention.

Examples

1. In Vivo Efficacy Studies in the AG129 Mouse Viremia Model Against DENV-2 with a High Viral Input ($10^6$ PFU), Using Compound (a) b.i.d. as Pre-Exposure Prophylaxis The AG129 mouse model is a well-established model to study the antiviral effect of compounds against DENV in vivo (Zompi and Harris, 2012). These 129/Sv mice are deficient for both IFN-α/β and IFN-γ receptors, enabling peripheral viral replication upon intravenous (i.v.) or subcutaneous (s.c.) infection with DENV (Johnson and Roehrig, 1999).

Several preclinical candidates, including celgosivir (an α-glucosidase inhibitor; Wathanebe et al, 2012 and Rathore et al., 2011) and NITD-008 (an adenosine nucleoside inhibitor; Yin et al., 2009) have been evaluated in this model.

Compound (a) of the present invention was tested in AG129 mouse viremia model. The synthesis of compound (a) is described in WO 2016/180696, under Example 9.

compound (a)

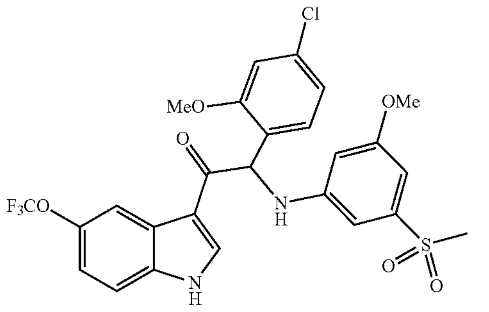

AG129 mice, age- and sex-matched (6 to 10 weeks of age), were used to assess the antiviral effect of compound (a) on viral RNA levels in the serum. Animals were infected intraperitoneally (i.p.) with high viral input of $10^6$ plaque-forming units (PFU) DENV-2/Rega lab strain. Animals were treated by administering compound (a) by oral gavage with a first administration at one hour prior to infection. The treatment continued for three consecutive days with one administration of compound (a) every 12 hours (twice daily or b.i.d.). At day 3 post infection (p.i.), the mice were sacrificed, and blood was collected and stored at −80° C. for viral load determination (FIG. 1).

The mice were divided in several groups (n=8/group) representing the following treatment regimens:

(i) vehicle 80%/20% PEG400/$H_2O$,
(ii) reference compound (2'CMC): 50 mg/kg/dose b.i.d., administered subcutaneously (s.c.),
(iii) compound (a): 30 mg/kg/dose b.i.d.
(iv) compound (a): 10 mg/kg/dose b.i.d.
(v) compound (a): 3 mg/kg/dose b.i.d.
(vi) compound (a): 1 mg/kg/dose b.i.d.
(vii) compound (a): 0.3 mg/kg/dose b.i.d. and
(viii) compound (a): 0.1 mg/kg/dose b.i.d.

Total RNA from serum was extracted using the NucleoSpin RNA virus kit according to the manufacturer's protocol (Macherey-Nagel, Düren, Germany). The viral RNA load was determined by one-step TaqMan RT-qPCR (master mix from Eurogentec, Seraing, Belgium).

A statistical analysis has been performed to estimate the mean viral RNA level over three experiments after treatment with compound (a). Results from the three experiments were pooled together. Two-way ANOVA model was used to estimate the mean viral RNA level.

Figure 2:
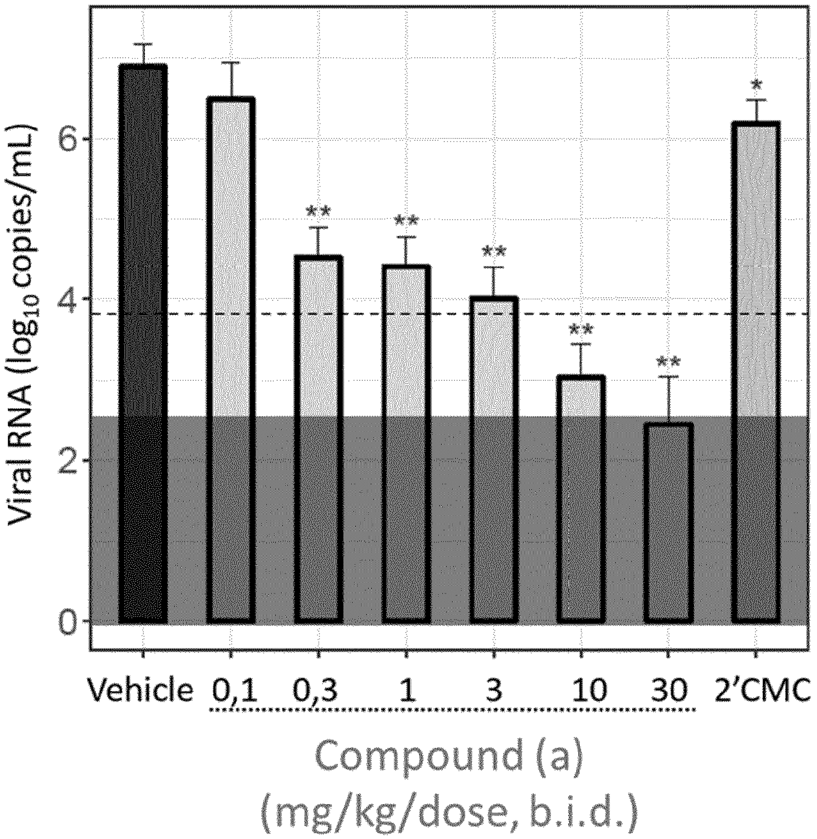
FIG. 2: Mean $\log_{10}$ Viral Load (copies/mL) in serum of DENV-2/Rega infected mice ($10^6$ PFU) treated b.i.d. with compound (a) at 0.1, 0.3, 1, 3, 10, and 30 mg/kg/dose twice daily (b.i.d.), per os (p.o.) in comparison with vehicle and 2'-C-Methylcytidine (2'CMC) b.i.d. treated mice at 3 days post infection (p.i.). Dotted line: Lower limit of quantification (LLOQ) (3.8 $\log_{10}$ copies/mL). Filled horizontal rectangle shown in the lower part of the figure: negative values: all negative values were imputed to a value of 2.6 $\log_{10}$ copies/mL, which corresponds with a Ct value of 40. Significant mean viral load reductions ($\log_{10}$ copies/mL) are indicated by stars (*$p<0.05$ and **$p<0.001$). A graphical representation of the estimated mean $\log_{10}$ viral load (copies/mL) values by treatment group together with the upper limit of the 95% confidence interval is shown.

A dose-dependent reduction in mean viral load was estimated for the dose-range of 0.1, 0.3, 1, 3, 10, and 30 mg/kg/dose b.i.d., compound (a) in serum (FIG. 2). All doses, except 0.1 mg/kg/dose b.i.d., resulted in a significant viral load reduction in serum compared with the vehicle-treated group ($p<0.001$). In serum at 30 mg/kg/dose b.i.d., a viral load reduction of 4.4 $\log_{10}$ copies/mL was observed, and at the lowest dose of compound (a) (0.1 mg/kg/dose b.i.d.), a viral load reduction of 0.47 $\log_{10}$ copies/mL was still achieved.

Figure 3:
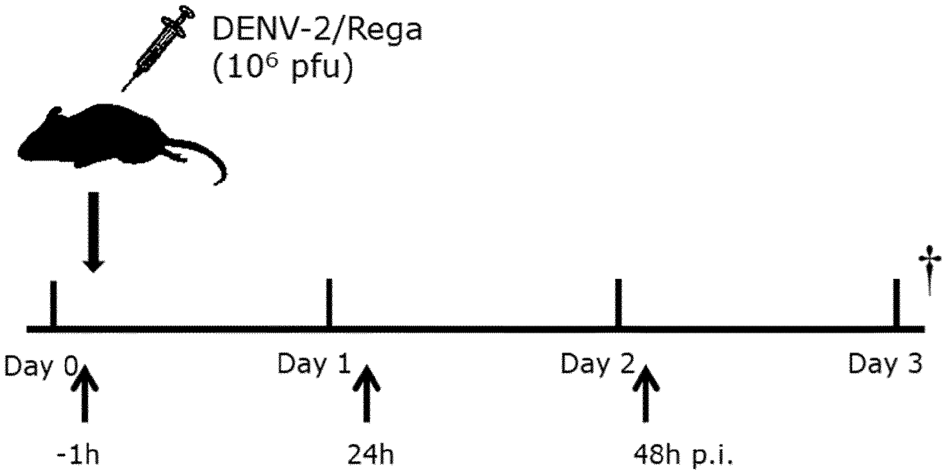
FIG. 3: Schematic representation of the in vivo viremia mouse experiment where compound (a) (q.d.) is tested for efficacy against a high viral input or inoculum of DENV-2/Rega ($10^6$ PFU). The arrows at the bottom of the figure show the q.d. administrations of compound (a)/vehicle p.o. At day 0, 1 hour after the first administration of compound (a), the mice were infected i.p. with $10^6$ PFU DENV-2/Rega.

2. In Vivo Efficacy Studies in the AG129 Mouse Viremia Model Against DENV-2 with a High Viral Input ($10^6$ PFU), Using Compound (a) q.d. As Pre-Exposure Prophylaxis In a similar setup as for the b.i.d. dosing studies, the in vivo efficacy was studied in the AG129 standard viremia model against DENV-2 with high viral inoculum and with compound (a) q.d. administration. Animals were i.p. infected with $10^6$ PFU DENV-2/Rega lab strain in a volume of 200 μL. Animals were treated by administering compound (a) by oral gavage with a first administration at one hour prior to infection. The treatment continued for three consecutive days with one administration of compound (a) every 24 hours (once a day or q.d.). At day 3 post infection (p.i.), the mice were euthanized, and blood was collected (FIG. 3). The viral RNA load was determined as outlined in example 1.

The mice were divided in 5 groups (n=8/group) representing the following treatment regimens:

(i) Vehicle 80%/20% PEG400/$H_2O$,
(ii) reference compound (2'CMC, 50 mg/kg per dose, b.i.d., s.c.),
(iii) compound (a): 0.3 mg/kg/dose q.d.
(iv) compound (a): 3 mg/kg/dose q.d.
(v) compound (a): 30 mg/kg/dose q.d.

Figure 4:
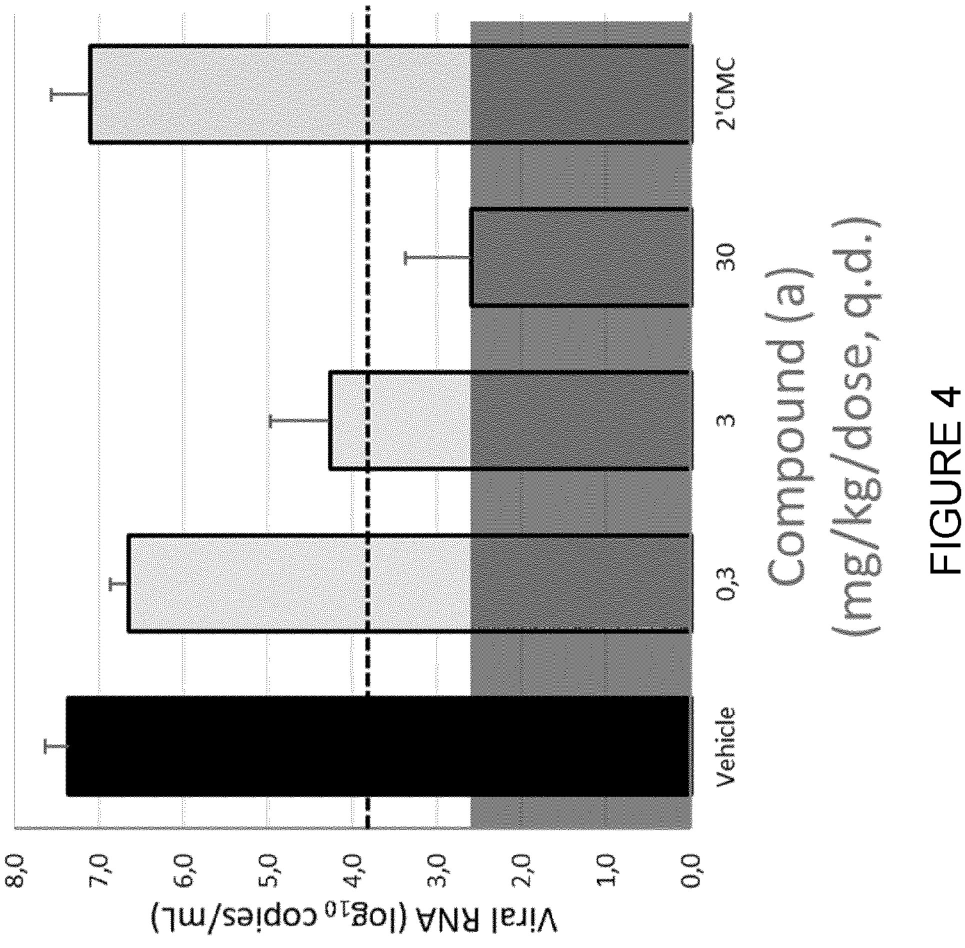
FIG. 4: Mean $\log_{10}$ Viral Load (copies/mL) in serum of DENV-2/Rega infected mice ($10^6$ PFU) treated q.d. with compound (a) at 0.3, 3 and 30 mg/kg/dose q.d. p.o. in comparison with vehicle, q.d. and 2'CMC, b.i.d. treated mice at 3 days p.i. Standard deviations are shown as error bars in the figure. Dotted line: Lower limit of quantification (LLOQ)=3.8 $\log_{10}$ copies/mL. Filled horizontal rectangle shown in the lower part of the figure: negative values: all negative values were imputed to a value of 2.6 log 10 copies/mL, which corresponds with a Ct value of 40.

A dose-dependent reduction in median viral load was observed at day 3 p.i. in serum. For the dose-ranges of 0.3, 3, and 30 mg/kg/dose q.d. of compound (a), respectively, median viral load reductions of 0.7, 3.1, and 4.5 $\log_{10}$ copies/mL were observed versus (vs.) vehicle-treated mice (FIG. 4).

3. In Vivo Efficacy Studies in the AG129 Mouse Viremia Model Against DENV-2 with a Low Viral Input ($10^2$ PFU), Using Compound (a) b.i.d. As Pre-Exposure Prophylaxis In this experiment, lower viral inputs were used ($10^2$ PFU), compared with the standard viremia experiments with a high viral input ($10^6$ PFU). $10^2$ PFU was selected as it was the lowest viral load leading to a Dengue infection in the mouse model. Using a lower viral input still results in 100% infection of the mice, but the peak viral load is postponed with 1 to 2 days, which more closely mimics a natural human infection (Clapham et al., 2014 and Sim et al., 2015). The mice were treated during 6 consecutive days.

Figure 5:
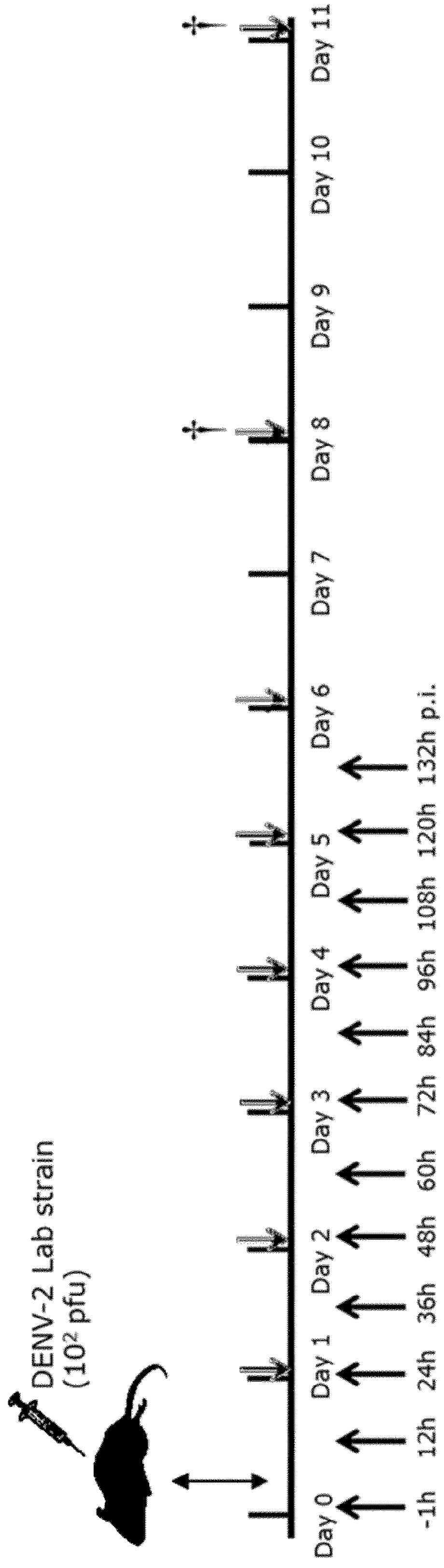
FIG. 5: Schematic representation of the in vivo viremia mouse experiment where compound (a) b.i.d. is tested for efficacy against a low viral input or inoculum of DENV-2/Rega ($10^2$ PFU). Arrows pointing up: b.i.d. administration of compound (a)/vehicle. Arrows pointing down: collection of blood samples to measure viral RNA load. At day 0, 1 hour after the first administration of compound (a), the mice were infected i.p. with $10^2$ PFU DENV-2/Rega.

Animals were infected i.p. with $10^2$ PFU DENV-2/Rega lab strain and treated for six consecutive days twice daily with compound (a) by oral gavage (FIG. 5).

The mice were divided in four treatment groups (n=16/group) representing the following treatment regimens:

(i) Vehicle 80%/20% PEG400/$H_2O$,
(ii) compound (a): 10 mg/kg/dose b.i.d. p.o.
(iii) compound (a): 1 mg/kg/dose b.i.d. p.o.
(iv) compound (a): 0.1 mg/kg/dose b.i.d. p.o.

Figure 6:
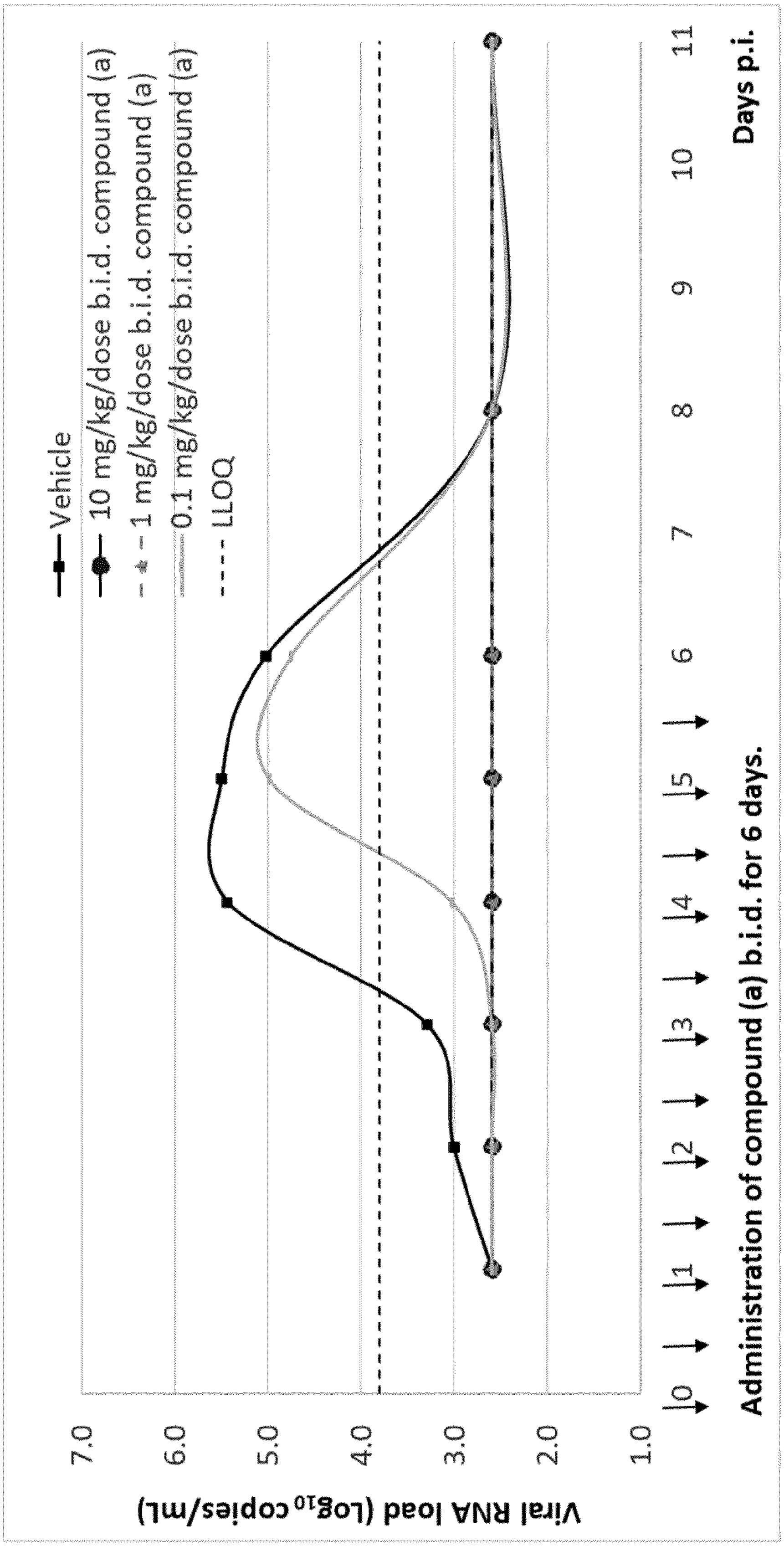
FIG. 6: Median $\log_{10}$ viral load (copies/mL) in serum of DENV-2/Rega infected mice ($10^2$ PFU) over 11 days; treated with compound (a) at 0.1, 1, and 10 mg/kg/dose b.i.d. in comparison with vehicle-treated mice. The arrows below the x-axis indicate b.i.d. administration of compound (a). Lowest limit of quantification (LLOQ)=3.8 $\log_{10}$ copies/mL. All negative values were imputed to a value of 2.6 $\log_{10}$ copies/mL, which corresponds with a Ct-value of 40.

Daily blood samples were collected to follow the viral load over time. Blood collection, for viral RNA load detection, was performed in two alternating sub-groups of mice. Each sub-group comprised half of the mice (n/2=8) from each of the treatment groups (i) to (iv). Blood was collected from a first sub-group at day 1, 3, 5 and 8 p.i. and from a second sub-group at day 2, 4, 6 and 11 p.i. At day 8 p.i., mice of the first sub-group were sacrificed while those of the second sub-group were sacrificed at day 11 p.i. Blood collection was always performed just before the next administration of the compound The vehicle-treated mice reached their peak viral load at day 4 to day 5 p.i., while for the mice treated with 0.1 mg/kg/dose b.i.d. compound (a), the peak was delayed by about ~1 day. At day 5, a dose of 0.1 mg/kg/dose b.i.d. compound (a) reduced the viral load with 0.50 $\log_{10}$ copies/mL compared with vehicle. The two higher doses (10 and 1 mg/kg/dose b.i.d. compound (a)) reduced the viral load in the mice, over all the days, to undetectable levels (FIG. 6).

Figure 7:
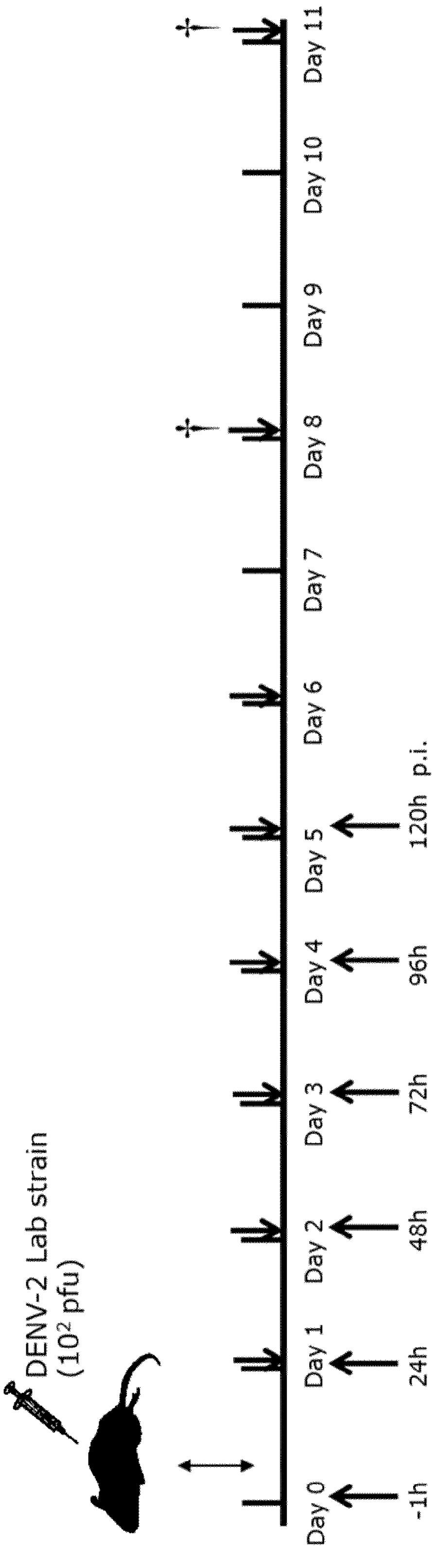
FIG. 7: Schematic representation of the in vivo viremia mouse experiment where compound (a) q.d. is tested for efficacy against a low viral input or inoculum of DENV-2/Rega ($10^2$ PFU). Arrows pointing up: q.d. administration of compound (a)/vehicle. Arrows pointing down: collection of blood samples to measure viral RNA load. At day 0, 1 hour after the first administration of compound (a), the mice were infected i.p. with $10^2$ PFU DENV-2/Rega.

4. In Vivo Efficacy Studies in the AG129 Mouse Viremia Model Against DENV-2 with a Low Viral Input ($10^2$ PFU), Using Compound (a) q.d. As Pre-Exposure Prophylaxis AG129 mice, age and sex matched (6 to 10 weeks of age), were used to assess the activity of compound (a) on viral RNA levels in serum. Animals were i.p. infected with $10^2$ PFU DENV-2/Rega lab strain in a volume of 200 μL. Animals were treated by administering compound (a) by oral gavage with a first administration at one hour prior to infection. The treatment continued for six consecutive days with one administration of compound (a) every 24 hours (once a day or q.d.) (FIG. 7).

Three independent experiments were performed. In each of the three experiments, three different doses of compound (a) were tested in addition to the vehicle. Mice were divided in 4 treatment groups (n=16/group) representing the following treatment regimens:

(i) Vehicle,
(ii) experiment 1: compound (a) administrated q.d. p.o. at 0.1, 0.6 and 30 mg/kg/dose q.d. (results in FIG. 8)
(iii) experiment 2: compound (a) administrated q.d. p.o. at 0.1, 0.3 and 1 mg/kg/dose q.d. (results in FIG. 9)
(iv) experiment 3: compound (a) administrated q.d. p.o. at 1, 3 and 10 mg/kg/dose q.d. (results in FIG. 10)

Alternating sub-groups were used to enable daily blood collections. Blood for viral RNA load detection was collected from mice in two alternating sub-groups. Each sub-group comprised half of the mice (n/2=8) from each of the treatment groups (i) to (iv). Blood was collected from a first sub-group at day 1, 3, 5 and 8 p.i. and from a second sub-group at day 2, 4, 6 and 11 p.i. Blood collection was always performed just before the next administration of the compound. At day 8 p.i., half of the mice in each treatment group (n=8/group) were sacrificed. The remaining mice in each treatment group (n=8/group) were sacrificed at day 11 p.i. (FIG. 7).

Figure 8:
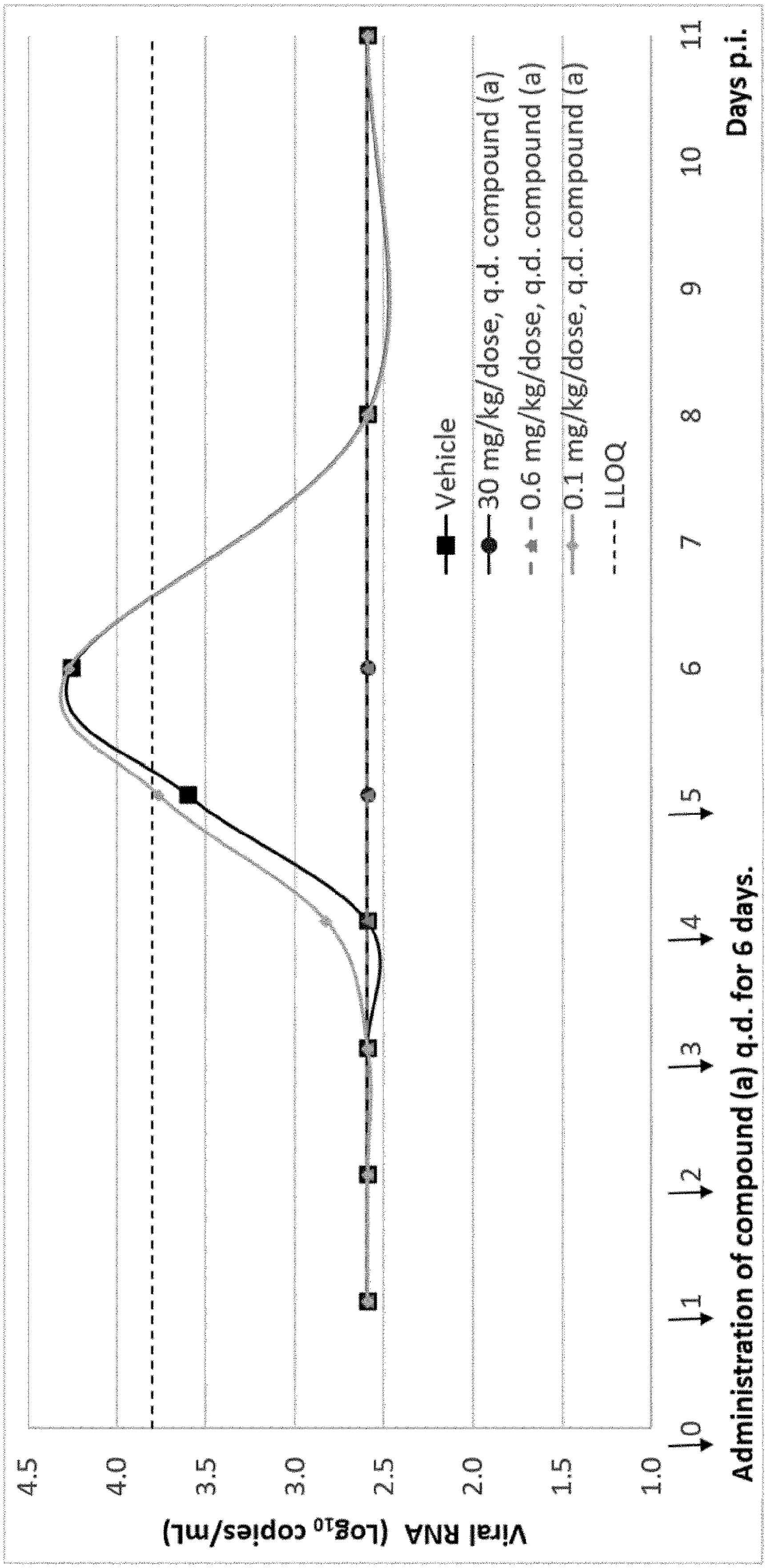
FIG. 8: Median $\log_{10}$ viral load (copies/mL) in serum of DENV-2/Rega infected mice ($10^2$ PFU) over 11 days; treated with compound (a) at 0.1, 0.6, and 30 mg/kg/dose q.d. in comparison with vehicle-treated mice. The arrows below the x-axis indicate q.d. administration of compound (a). Lowest limit of quantification (LLOQ)=3.8 $\log_{10}$ copies/mL. All negative values were imputed to a value of 2.6 $\log_{10}$ copies/mL, which corresponds with a Ct-value of 40.
Figure 9:
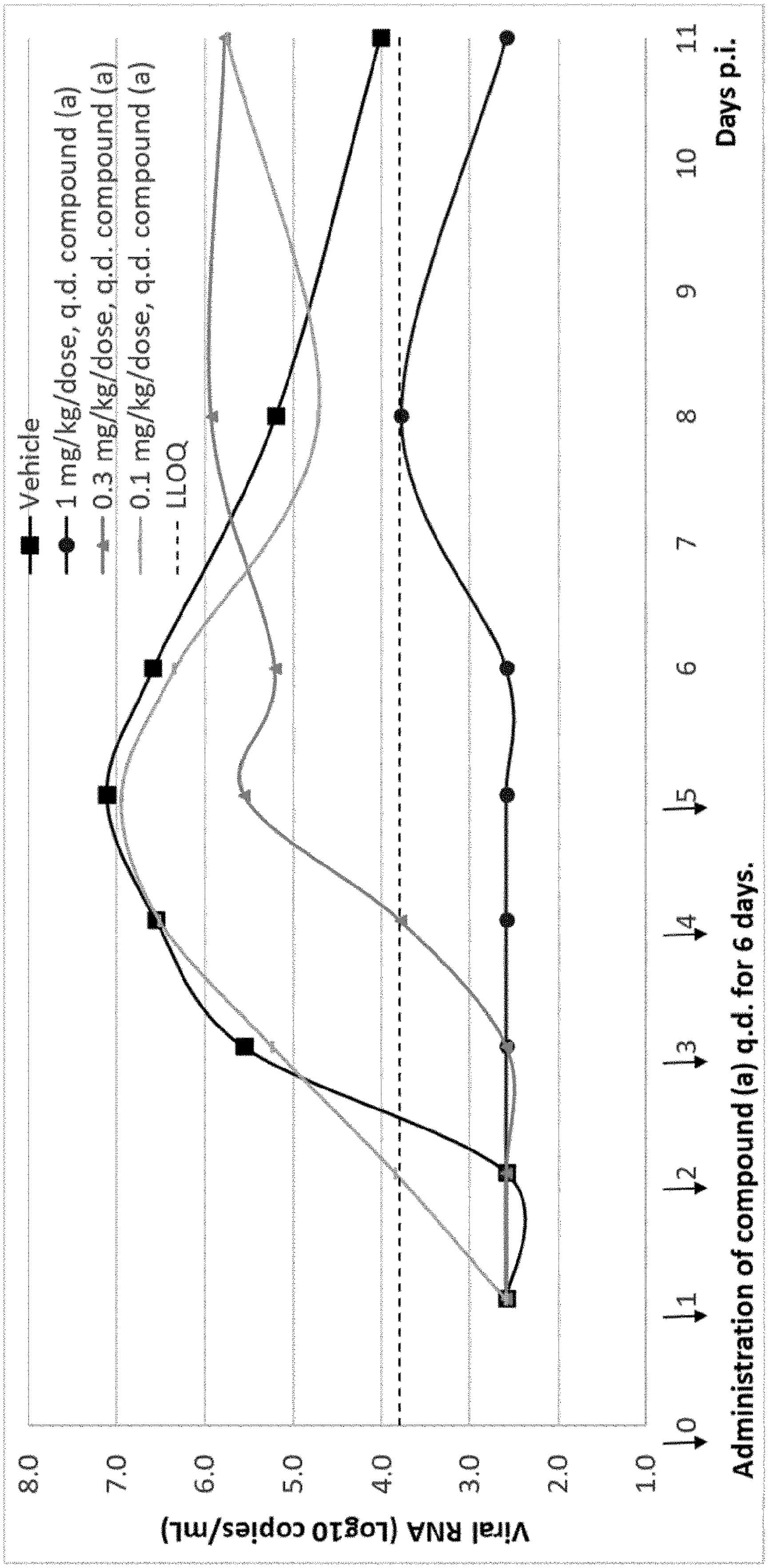
FIG. 9: Median $\log_{10}$ viral load (copies/mL) in serum of DENV-2/Rega infected mice ($10^2$ PFU) over 11 days; treated with compound (a) at 0.1, 0.3, and 1 mg/kg/dose q.d. in comparison with vehicle-treated mice. The arrows below the x-axis indicate q.d. administration of compound (a). Lowest limit of quantification (LLOQ)=3.8 $\log_{10}$ copies/mL. All negative values were imputed to a value of 2.6 $\log_{10}$ copies/mL, which corresponds with a Ct-value of 40.
Figure 10:
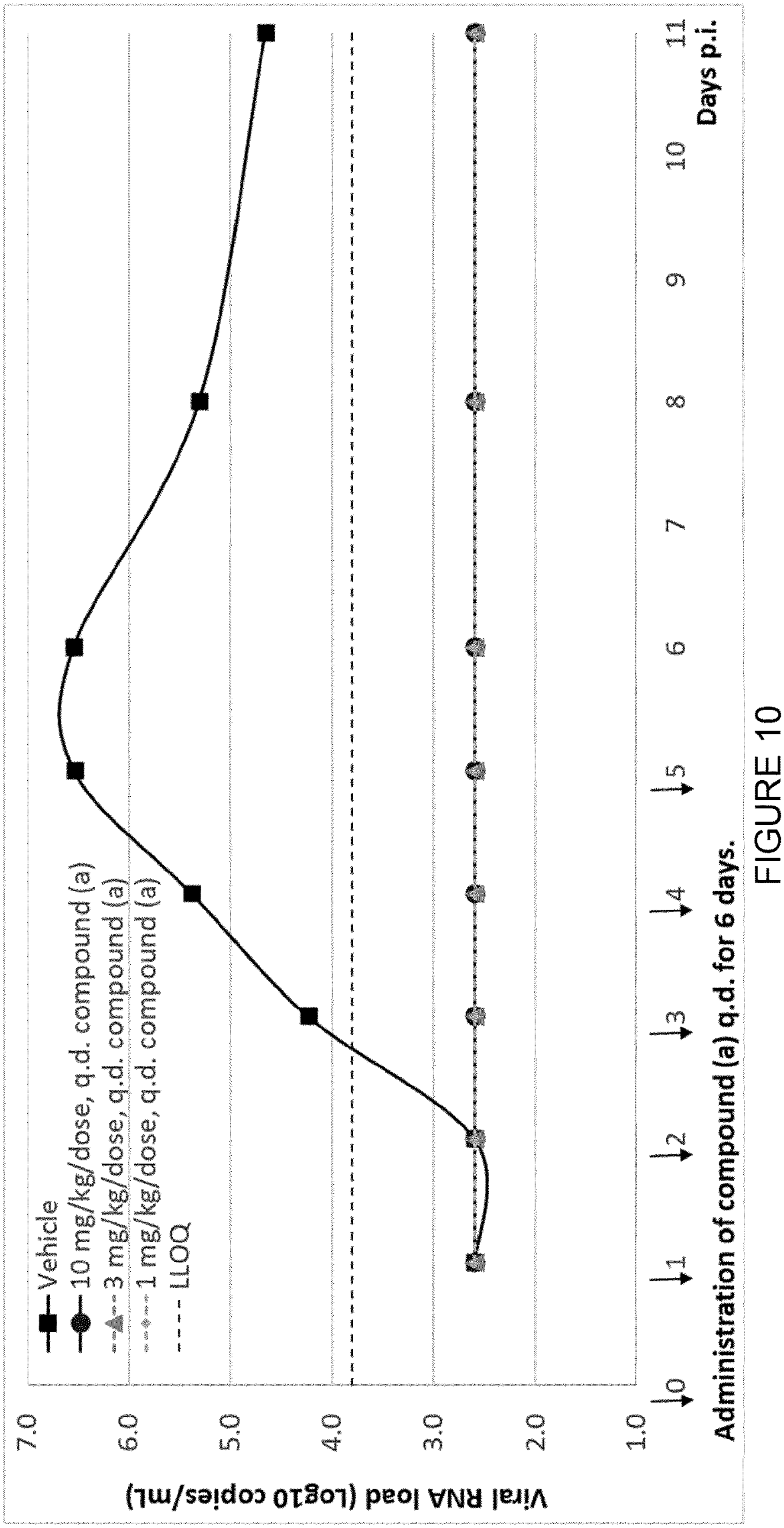
FIG. 10: Median $\log_{10}$ viral load (copies/mL) in serum of DENV-2/Rega infected mice ($10^2$ PFU) over 11 days; treated with compound (a) at 1, 3, and 10 mg/kg/dose q.d. in comparison with vehicle-treated mice. The arrows below the x-axis indicate q.d. administration of compound (a). Lowest limit of quantification (LLOQ)=3.8 $\log_{10}$ copies/mL. All negative values were imputed to a value of 2.6 $\log_{10}$ copies/mL, which corresponds with a Ct-value of 40.

Over the three experiments, the vehicle-treated mice reached peak viral load generally at day 5 to days 6 p.i. with median viral loads of 4.3, 7.1, and 6.6 $\log_{10}$ copies/mL, respectively, in experiments 1, 2, and 3 (FIG. 8, FIG. 9, and FIG. 10, respectively). Five of the 7 doses, i.e. 0.6, 1, 3, 10, and 30 mg/kg/dose q.d., of compound (a) reduced the median serum viral load in the mice over all 11 days to undetectable levels (LOD=2.59 $\log_{10}$ copies/mL) with 1 viral rebound at day 8 (median viral load of 3.78 $\log_{10}$ copies/mL) at 1 mg/kg/dose q.d. At 0.3 mg/kg/dose q.d., a viral load reduction of 1.6 $\log_{10}$ copies/mL was reached at day 5 compared to vehicle-treated mice, however, no further decline in viral load up to day 11 could be observed. At the lowest dose, 0.1 mg/kg/dose q.d, viral load over time was comparable to the vehicle-treated viral load curve.

5. Pre-Exposure Prophylaxis with Compound (a) q.d. In a Non-Human Primate Model (*Macaca mulatta*) Against DENV-2/16681.

Figure 11:
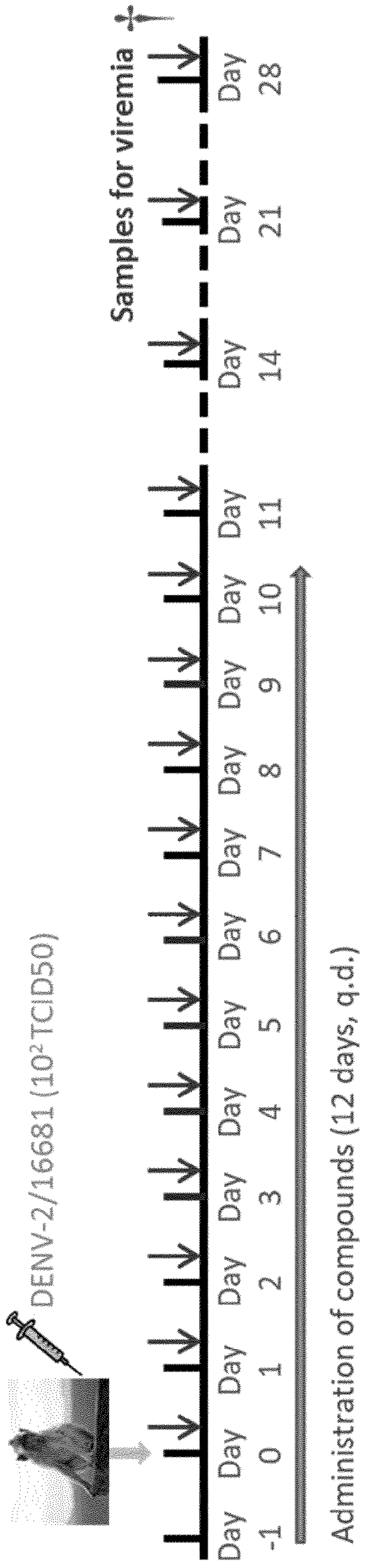
FIG. 11: Schematic representation of the in vivo Non-Human Primate (NHP) experiment where rhesus macaques were infected with a viral inoculum of $10^2$ $TCID_{50}$ DENV-2/16681. The horizontal arrow indicates q.d. administration of compound (a)/vehicle from day −1 until and including Day 10. Dark grey arrows pointing down: collection of blood samples to measure viral RNA load.

Compound (a) was tested in a non-human primate (NHP) model against DENV-2/16681. The setup of the experiment was designed as a pre-exposure prophylaxis (PreP) study. Oral administration of compound (a) started one day before experimental infection (day −1) and continued with daily administrations until 10 days post-infection. On day 0, the animals were infected by intradermal inoculation with 100 $TCID_{50}$ of DENV-2/16681 virus in a total volume of 0.1 mL (FIG. 11).

The rhesus monkeys were divided in 7 groups representing the following treatment regimens:

(i) Vehicle 100% PEG400 (n=5)
(ii) Group 1: 0.01 mg/kg/dose, q.d. (n=3),
(iii) Group 2: 0.18 mg/kg/dose, q.d. (n=3),
(iv) Group 3: 3 mg/kg/dose, q.d. (n=3),
(v) Group 4: 0.024 mg/kg/dose, q.d. (n=4),
(vi) Group 5: 0.09 mg/kg/dose, q.d. (n=4),
(vii) Group 6: 0.93 mg mg/kg/dose, q.d. (n=4).

Figure 12A:
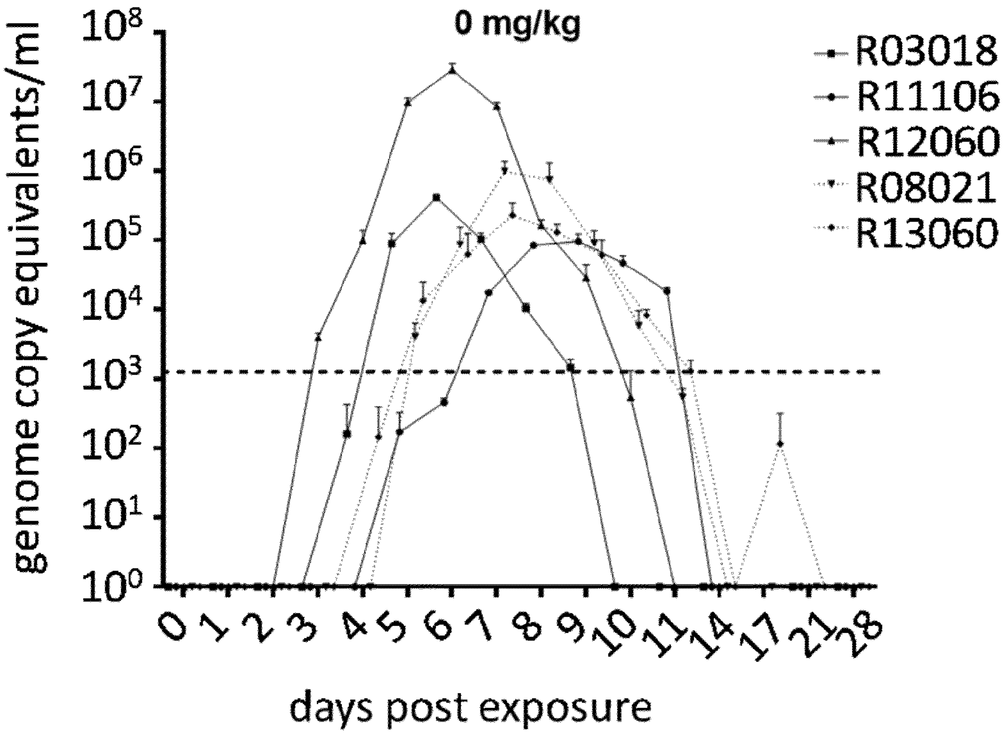
FIGS. 12 A and B: $\text{Log}_{10}$ viral RNA (GCE/mL) in serum of DENV-2/16681 infected rhesus monkeys (infected with $10^2$ $TCID_{50}$ DENV-2/16681); treated for 12 days with compound (a) at 0.01; 0.024; 0.09; 0.18; 0.93 and 3 mg/kg/dose q.d. in comparison with vehicle-treated rhesus monkeys (0 mg/kg/dose q.d.). Oral dosing of compound (a) was started 1 day before infection with DENV-2 and continued with daily dosing until 10 days post inoculation. The grey dashed line represents the lowest limit of quantification (LLOQ) of the assay (1286 RNA genome copy equivalents (GCE/mL). All negative values were imputed to a value of 42 GCE/mL, which corresponds with a Ct-value of 35.

The antiviral activity of compound (a) in a prophylactic setting is being assessed in DENV-2/16681 infected rhesus monkeys (*Macaca mulatta*). Blood samples were taken on a daily basis from day 0 until day 11, and on day 14 and day 28. DENV RNA was measured using real-time qPCR as described by Santiago et al. (2013). Results from compound (a) doses of 0.01, 0.024, 0.09, 0.18, 0.93 and 3 mg/kg, administered once daily from day 1 before infection until day 10 post infection, are shown in FIGS. 12A and B.

Figure 12B:
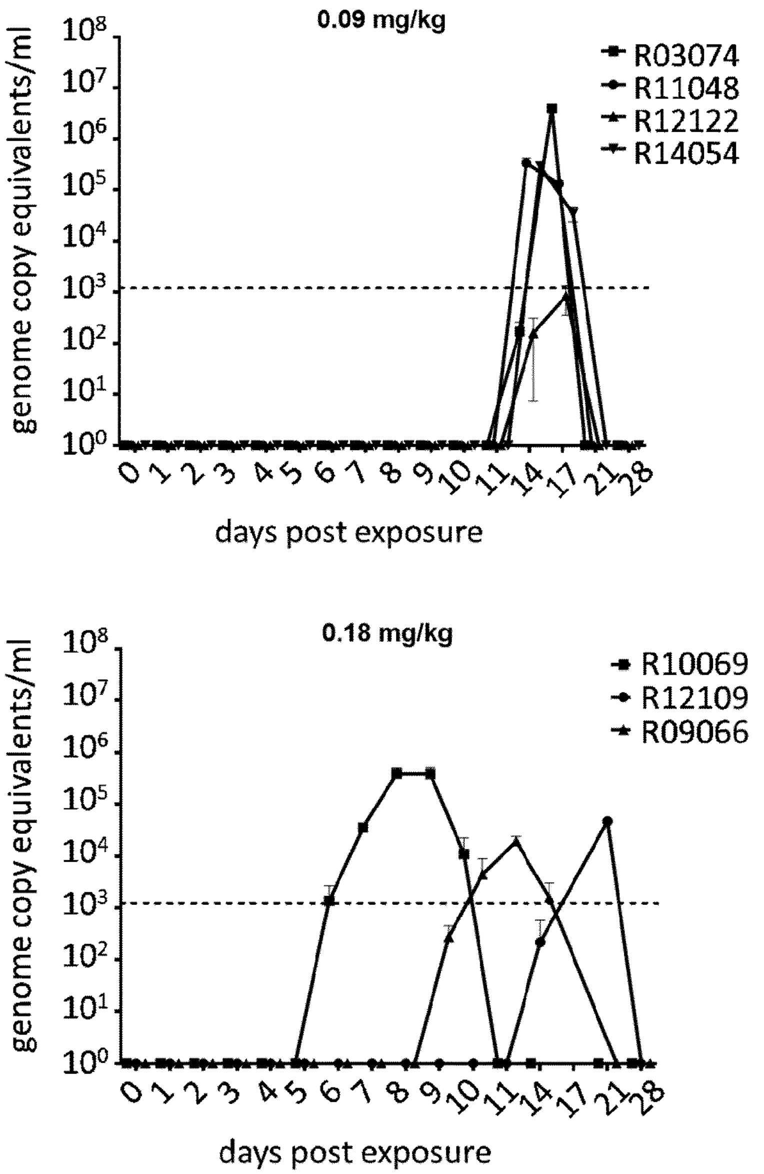

No DENV RNA was detectable throughout the study period, i.e. up to day 28 post dose, for the two highest doses (0.93 and 3 mg/kg dose). A delayed onset of DENV RNA and peak RNA was observed in some animals in the 0.09 and 0.18 mg/kg dosing groups (FIG. 12B). Data is shown for each individual animal (each line represents data from one animal). The dashed horizontal line at 1286 GCE/mL represents the lowest limit of quantification (LLOQ) of the assay (FIGS. 12A and B).

Based on a Bayesian nonlinear dose-response statistical model, the peak viral load reduction compared with vehicle was estimated for each dose group. No statistically significant reduction in median peak DENV RNA compared with vehicle was observed for the two lowest doses of 0.01 and 0.024 mg/kg. A dose dependent median reduction in DENV peak RNA levels of 0.78, 1.91, 4.73 and 6.76 $\log_{10}$ genome copy equivalents (GCE) per milliliter (GCE/mL) plasma compared with vehicle control was estimated with the 0.09, 0.18, 0.93 and 3 mg/kg doses, respectively (Table 1).

TABLE 1

The Median Estimated Change in Peak Viral Load (on $\log_{10}$ Scale) Versus Vehicle by Dose Group.

| Dose groups | Change in median PVL versus vehicle ($\log_{10}$) [95% credibility interval] |
|---|---|
| 3 mg/kg* | −6.76 [−8.87; −5.31] |
| 0.93 mg/kg* | −4.73 [−6.17; −3.72] |
| 0.18 mg/kg* | −1.91 [−2.67; −1.14] |

TABLE 1-continued

The Median Estimated Change in Peak Viral Load (on $Log_{10}$ Scale) Versus Vehicle by Dose Group.

| Dose groups | Change in median PVL versus vehicle ($log_{10}$) [95% credibility interval] |
|---|---|
| 0.09 mg/kg* | −0.78 [−1.48; −0.19] |
| 0.024 mg/kg | −0.02 [−0.33; 0.28] |
| 0.01 mg/kg | 0.001 [−0.302; 0.310] |

*Statistically significant reduction in median peak viral load of the dose group compared with vehicle (credibility interval of 95%).

6. Antiviral Activity of Compound (a) Against DENV 1/45AZ5 in Non-human Primates (*Macaca mulatta*).

Figure 13:
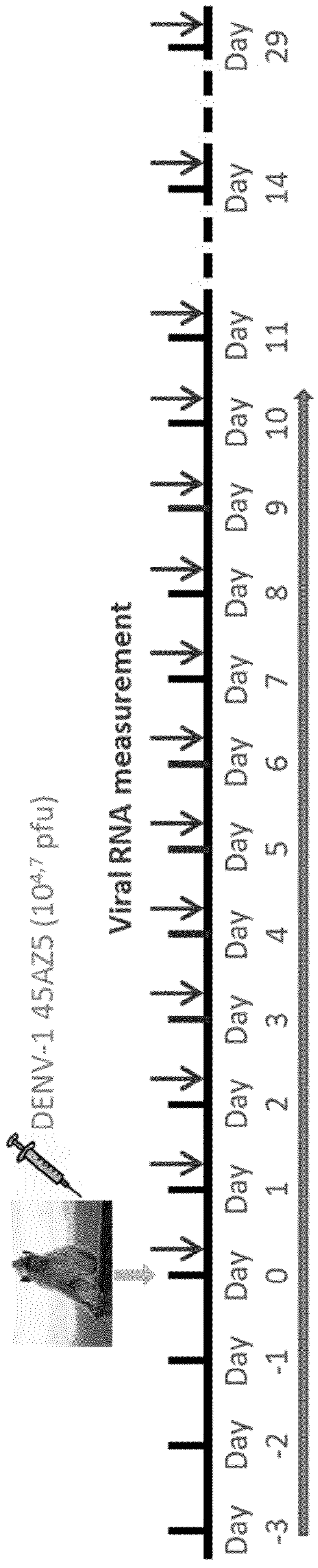
FIG. 13: Schematic representation of in vivo Non-Human Primate (NHP) experiment where rhesus macaques were infected at day 0, with 0.5 mL of DENV-1/45AZ5 (titer of $1.2\times10^5$ PFU/mL). The horizontal arrow indicates q.d. administration of compound (a)/vehicle from day −3 until and including Day 10. Dark grey arrows pointing down: collection of blood samples to measure viral RNA load.

The antiviral activity of compound (a) DENV in a prophylactic setting was assessed in rhesus monkeys (*Macaca mulatta*) infected with strain DENV 1/45AZ5. Oral dosing of compound (a) (6 mg/kg) was started 3 days before infection with DENV (day −3) and continued with daily dosing until 10 days post infection. On day 0, the animals were intradermally inoculated with 0.5 mL of DENV 1/45AZ5 (1.2×105 plaque-forming units [PFU/mL]). Animals were followed up until day 28 post infection (FIG. 13 X).

The rhesus monkeys were divided in 2 groups representing the following treatment regimens:

(i) Vehicle 100% PEG400 (n=6)

Figure 14X:
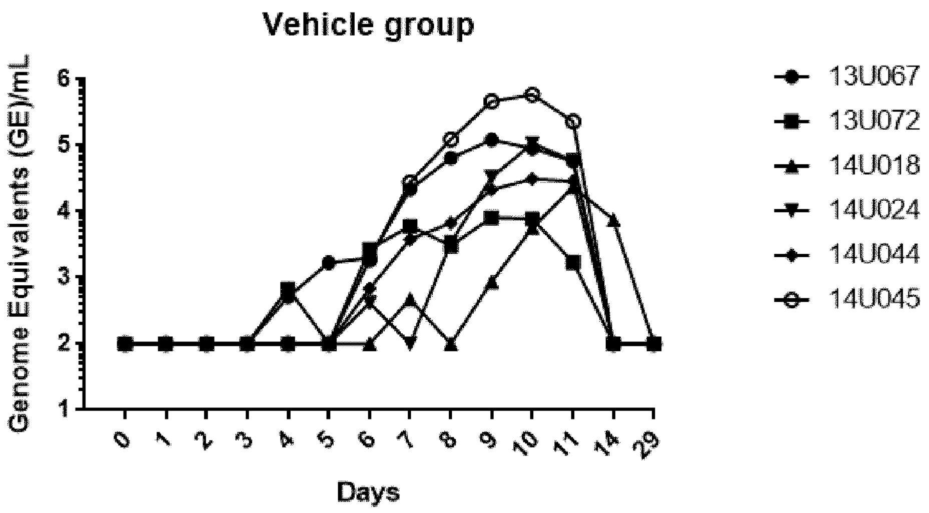
FIG. 14: $Log_{10}$ viral RNA (GCE/mL) in serum of DENV-1/45AZ5 infected rhesus monkeys ($10^{4.7}$ PFU), treated for 14 days with compound (a) at 6 mg/kg/dose q.d. (Y) in comparison with vehicle-treated rhesus monkeys (0 mg/kg/dose q.d.) (X) Oral dosing of compound (a) (6 mg/kg) was started 3 days before infection with DENV-1 and continued with daily dosing until 10 days post infection. The assay limit of quantification (LOQ) is 100 genomic copies/reaction.

(ii) Group 1: 6 mg/kg/dose, q.d. (n=6),

All animals in the vehicle control group had detectable DENV RNA starting from 4 days after virus challenge until day 14, with peak RNA ranging from 8.15×103 to 5.88×105 genome equivalents per mL (see FIG. 14X). Viral RNA for individual animals generally peaked between days 9 and 10 post challenge, and viral RNA was last detected on day 11, except for 1 animal (AID14U018) in the placebo group that was still DENV-RNA-positive on day 14.

Figure 14Y:
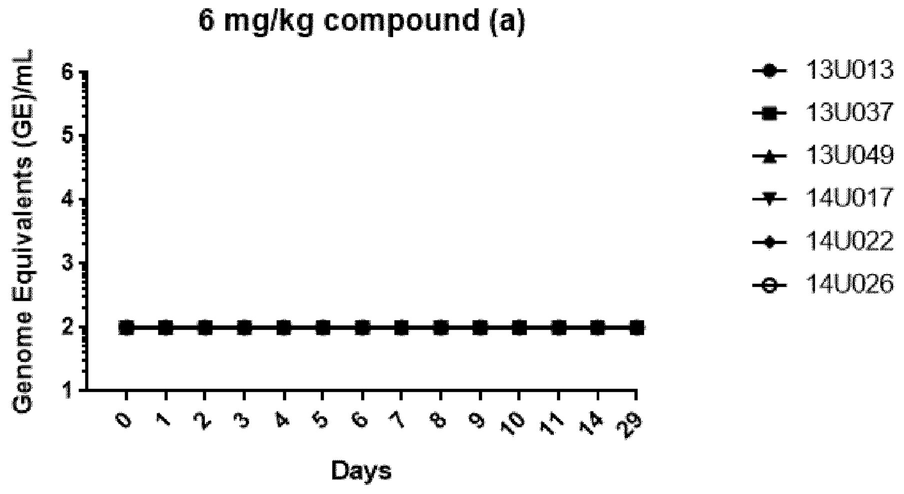

In compound (a) treated animals, DENV RNA remained undetectable during the complete study period (see FIG. 14Y).

7. In Vivo Efficacy Studies in the AG129 Mouse Viremia Model Against DENV-2 with a High Viral Input ($10^6$ PFU), Using Compound (b) b.i.d. As Pre-Exposure Prophylaxis Compound (b) of the present invention was tested in AG129 mouse viremia model. The synthesis of compound (b) is described in WO 2017/167951, under Example 4.

compound (b)

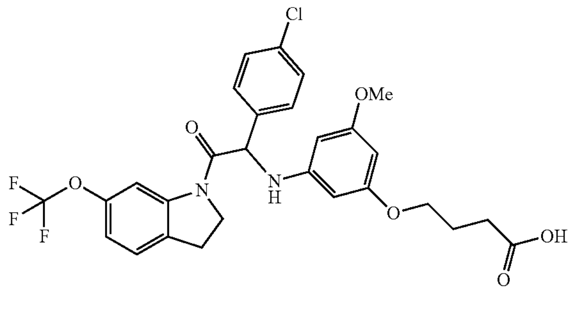

AG129 mice, age- and sex-matched (6 to 9 weeks of age), were used to assess the activity of compound (b) on viral RNA levels in the serum of the mice and on virus-induced disease or mortality of the mice.

Figure 15X:
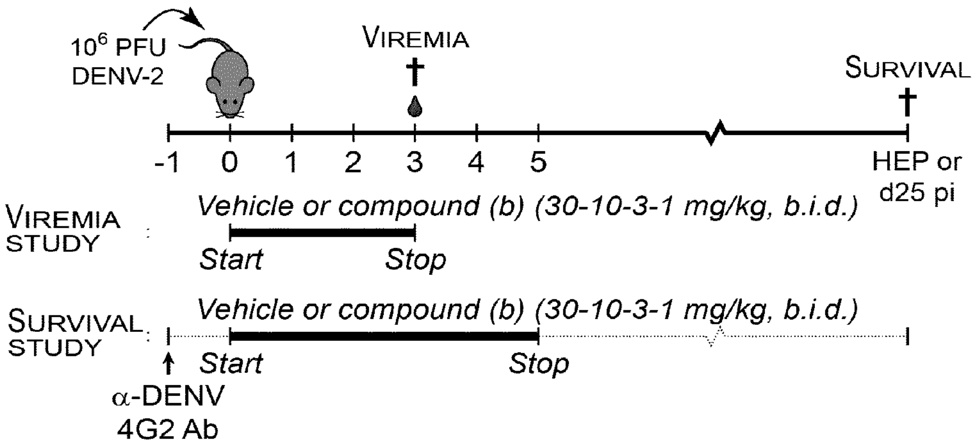
FIG. 15: In vivo efficacy of compound (b) on viremia and disease development in a prophylactic setting. X: Schematic outline of viremia and survival studies. Y: Inhibitory effect of compound (b) on viremia on day 3 p.i. and Z: virus-induced disease in mice treated twice-daily with 30 mg/kg, 10 mg/kg, 3 mg/kg or 1 mg/kg of compound (b), as compared to vehicle-treated mice (black dots). Data are compiled from two independently performed studies with n=8 (viremia) or n=10 (survival) per group. Statistical analysis was performed using the Kruskal-Wallis test (viremia) or the Log rank test (survival). *$P<0.05$; $P<0.01$; *$P<0.001$; ****$P<0.0001$; as compared to vehicle-treated mice. LLOQ, Lowest limit of quantification=3.8 $\log_{10}$ copies/mL. All negative values were imputed to a value of 2.6 $\log_{10}$ copies/mL, which corresponds with a Ct-value of 40.

For the viremia study, the animals were infected intraperitoneally (i.p.) with $1\times10^6$ plaque-forming units (PFU) DENV-2/Rega lab strain. Animals (n=8/group) were treated by administering compound (b) by oral gavage with a first administration at one hour prior to infection. The treatment continued for three consecutive days with one administration of compound (b) every 12 hours (twice daily or b.i.d.). At day 3 p.i., the mice were sacrificed, and blood was collected and stored at −80° C. for viral load determination (FIG. 15X). Total RNA from serum was extracted using the NucleoSpin RNA virus kit according to the manufacturer's protocol (Macherey-Nagel, DQren, Germany). The viral RNA load was determined by RT-qPCR as described above.

In the lethal DENV challenge study (or survival study), antibody-dependent-enhancement (ADE) induced dengue disease is imitated by injecting AG129 mice (n=10 per group) i.p. with Anti-Flavivirus Group Antigen Antibody, clone D1-4G2-4-15 ('4G2'; Millipore), one day prior to challenge with DENV-2 Rega lab strain ($1\times10^6$ PFU, i.p.). Animals were treated by administering compound (b) by oral gavage with a first administration at one hour prior to infection. The treatment continued for five consecutive days with one administration of compound (b) every 12 hours (twice daily or b.i.d.). (FIG. 15X).

The mice were divided in several groups (n=8/group for the viremia study and n=10/group for the survival study) representing the following treatment regimens:

(i) vehicle, 80%/20% PEG400/$H_2O$ (ii) compound (b): 30 mg/kg/dose b.i.d.

(iii) compound (b): 10 mg/kg/dose b.i.d.

(iv) compound (b): 3 mg/kg/dose b.i.d.

(v) compound (b): 1 mg/kg/dose b.i.d.

Figure 15Y:
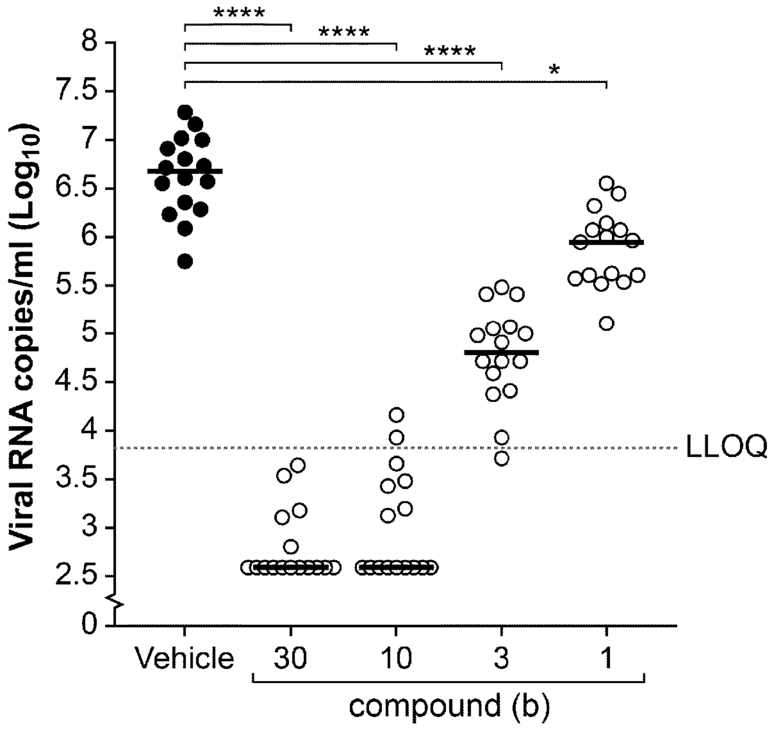

In the viremia study, a dose-dependent reduction in mean viral load in serum was observed for the tested dose regimens of 1, 3, 10 and 30 mg/kg per dose, b.i.d., compound (b). All four doses resulted in a significant viral load reduction compared with the vehicle-treated group ($p<0.05$). In the serum of the animals treated with 30 mg/kg per dose, b.i.d., a viral load reduction of 3.8 $log_{10}$ copies/mL was observed. At the lowest dose (1 mg/kg per dose, b.i.d.), a viral load reduction of 0.70 $log_{10}$ copies/mL was still achieved (FIG. 15Y).

Figure 15Z:
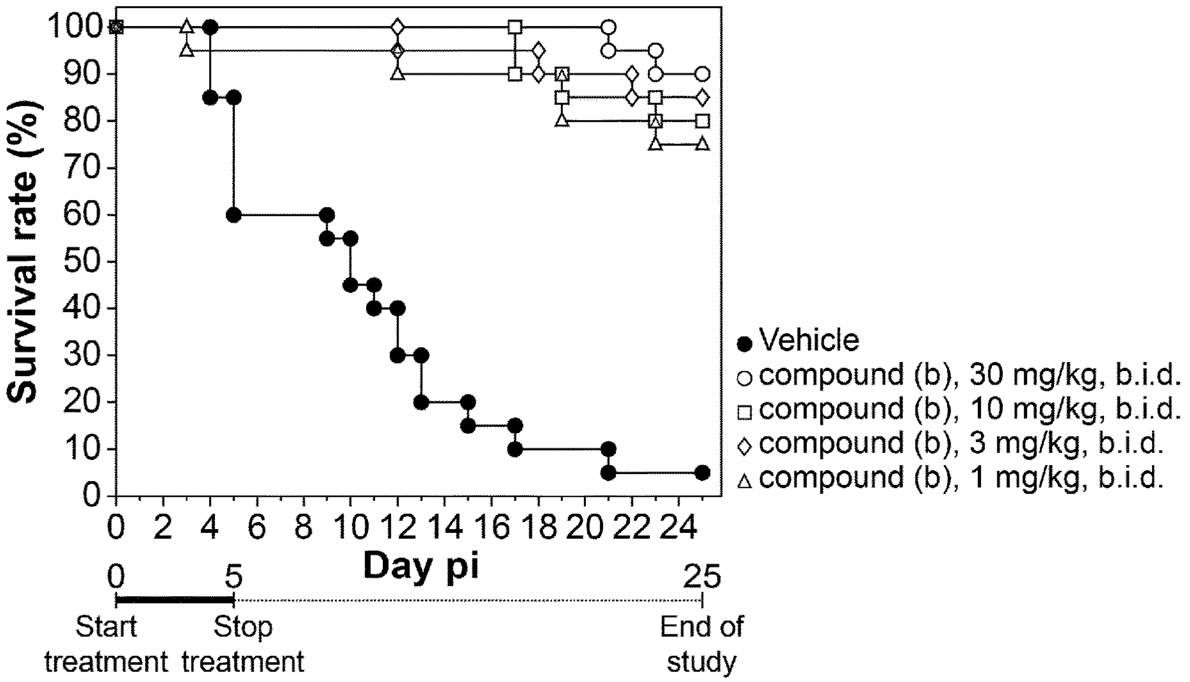

Next, the impact of compound (b) was assessed on virus-induced disease and mortality when dosed (orally, b.i.d.) for just 5 consecutive days starting at the day of infection (survival study). Animals were monitored for a maximum period of 25 days. All but one (19 of 20) vehicle-treated mice had to be euthanized. At a dose of 30 mg/kg, 90% of the mice survived the viral challenge and at doses of 10, 3 and 1 mg/kg, the survival rate was respectively 80%, 85% and 75% (FIG. 15Z).

Figure 16Y:
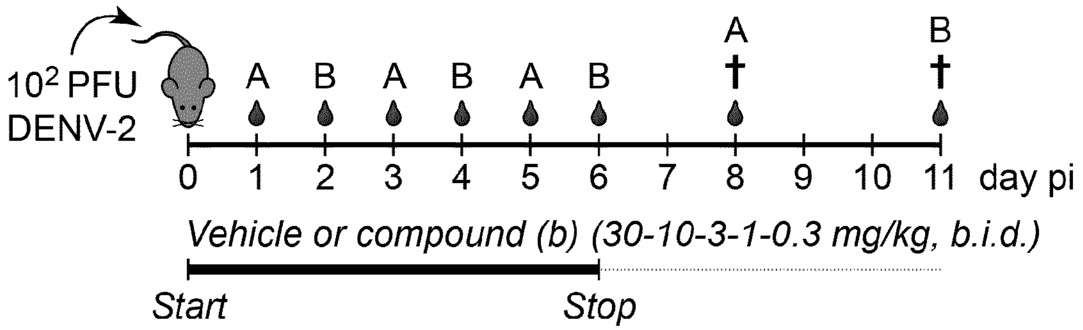
FIG. 16: In vivo efficacy of compound (b) on kinetics of DENV replication in a prophylactic setting. Y: Schematic outline of the in vivo kinetic studies. Each treatment group was divided in two sub-groups (n=8, each) for blood collection on alternating days. Z: Inhibitory effect of compound (b) on viremia on various days p.i. in mice treated twice-daily with 30 mg/kg (white dots, n=8), 10 mg/kg (light grey dots, n=8), 3 mg/kg (light grey dots, n=16), 1 mg/kg (light grey dots, n=8), or 0.3 mg/kg (light grey dots, n=8) compound (b), as compared to vehicle-treated mice (black dots, n=16). Data are compiled from two independently performed studies. LLOQ, Lowest limit of quantification=3.8 $\log_{10}$ copies/mL. All negative values were imputed to a value of 2.6 $\log_{10}$ copies/mL, which corresponds with a Ct-value of 40.

8. In Vivo Efficacy Studies in the AG129 Mouse Viremia Model Against DENV-2 with a Low Viral Input ($10^2$ PFU), Using Compound (b) b.i.d. As Pre-Exposure Prophylaxis AG129 mice, age and sex matched (6 to 10 weeks of age), were used to assess the activity of compound (b) on viral RNA levels in serum. Animals were i.p. infected with $10^2$ PFU DENV-2/Rega lab strain in a volume of 200 μL. Animals were treated by administering compound (b) by oral gavage with a first administration at one hour prior to infection. The treatment continued for six consecutive days with one administration of compound (b) every 12 hours (twice daily or b.i.d.) (FIG. 16 Y).

Five different doses of compound (b) were tested in addition to the vehicle. Mice were divided in 6 treatment groups (n=16/group) representing the following treatment regimens:

(i) Vehicle,
(ii) compound (b) administrated b.i.d. p.o. at 0.3 mg/kg/dose b.i.d.,
(iii) compound (b) administrated b.i.d. p.o. at 1 mg/kg/dose b.i.d.,
(iv) compound (b) administrated b.i.d. p.o. at 3 mg/kg/dose b.i.d.,
(v) compound (b) administrated b.i.d. p.o. at 10 mg/kg/dose b.i.d.,
(vi) compound (b) administrated b.i.d. p.o. at 30 mg/kg/dose b.i.d.

Alternating sub-groups were used to enable daily blood collections. Blood for viral RNA load detection was collected from mice in two alternating sub-groups. Each sub-group comprised half of the mice (n/2=8) from each of the treatment groups (i-vi). Blood was collected from a first sub-group at days 1, 3, 5 and 8 p.i. and from a second sub-group at days 2, 4, 6 and 11 p.i. Blood collection was always performed just before the next administration of the compound. At day 8 p.i., half of the mice in each treatment group (n=8/group) were sacrificed. The remaining mice in each treatment group (n=8/group) were sacrificed at day 11 p.i (FIG. 16 Y).

Figure 16Z:
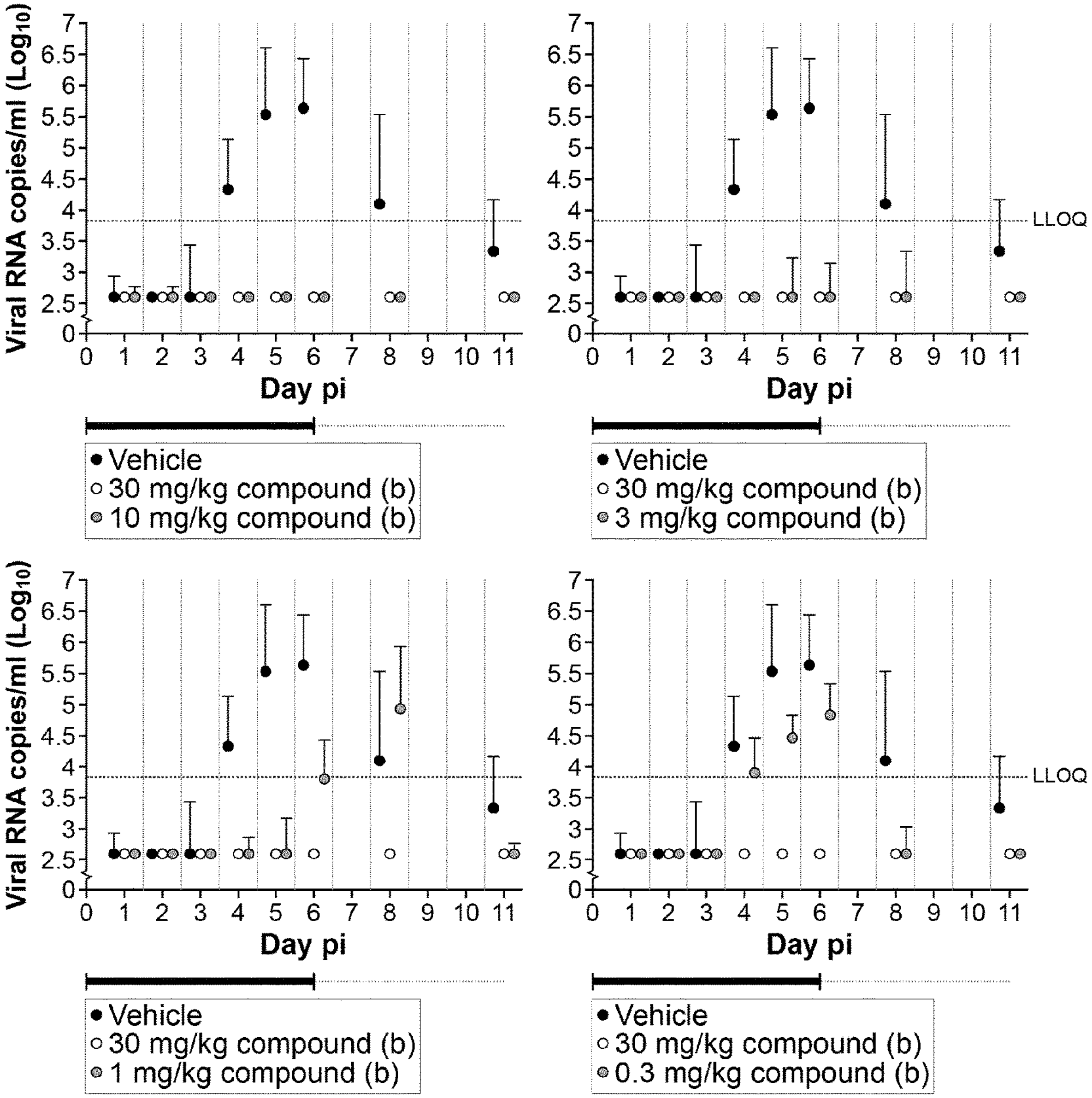

Doses of either 30, 10 or 3 mg/kg/dose, b.i.d of compound (b) reduced viral RNA levels to undetectable levels (FIG. 16Z). Even at doses as low as 1 and 0.3 mg/kg viral RNA levels at peak viremia were reduced by respectively 1.8 $log_{10}$ and 0.8 $log_{10}$ (FIG. 16Z).

9. PrEP, Post Exposure Prophylaxis (PEP) and Treatment with Compound (b) in an In Vivo AG129 Mouse Model Against DENV-2/Rega AG129 mice, age- and sex-matched (6 to 9 weeks of age), were used to assess the activity of compound (b) on viral RNA levels in the serum of the mice. The animals were infected intraperitoneally (i.p.) with $1\times10^2$ PFU DENV-2/Rega lab strain and treated for five consecutive days with compound (b) which was administered by oral gavage. Compound (b) was administered every 12 hours (twice daily or b.i.d.).

The mice were divided in six treatment groups (n=8/group) representing the following treatment regimens:
(i) Vehicle 80%/20% PEG400/$H_2O$ (group 1),
(ii) 30 mg/kg/dose compound (b) b.i.d.: first administration 1 hour before infection (group 2),
(iii) 30 mg/kg/dose compound (b) b.i.d., first administration 1 day after infection (group 3),
(iv) 30 mg/kg/dose compound (b) b.i.d., first administration 2 days after infection (group 4),
(v) 30 mg/kg/dose compound (b) b.i.d., first administration 3 days after infection (group 5),
(vi) 30 mg/kg/dose compound (b) b.i.d., first administration 4 days after infection (group 6),
(vii) 30 mg/kg/dose compound (b) b.i.d., first administration 5 days after infection (group 7),
(viii) 30 mg/kg/dose compound (b) b.i.d., first administration 6 days after infection (group 8).

Figure 17Y:
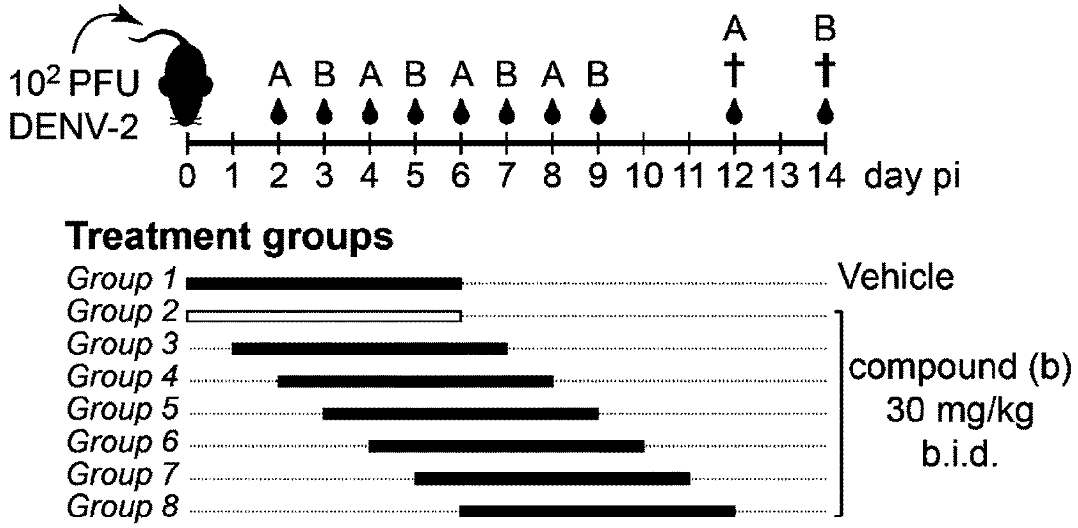
FIG. 17: In vivo efficacy of compound (b) on kinetics of DENV replication in a Post-Exposure Prophylaxis (PEP) and therapeutic setting. Y: Schematic outline of the in vivo kinetic studies whereby treatment was started on day 1-5 after DENV challenge (groups 3-7). In control groups, treatment was started on the day of infection (groups 1-2). Each treatment group (n=8, each) was divided in two sub-groups (n=4, each) for blood collection on alternating days. Z: Inhibitory effect of compound (b) on viremia at various time points p.i. in mice treated twice-daily with 30 mg/kg for 6 consecutive days. In the delayed treatment groups (group 3-8), treatment with compound (b) was started on day 1 (group 3), day 2 (group 4), day 3 (group 5), day 4 (group 6), day 5 (group 7), or day 6 (group 8). As controls, two groups of mice received treatment on the day of infection: group 1 (vehicle; black filled dots/bar) and group 2 (compound (b); white empty dots/bar). LLOQ, Lowest limit of quantification=3.8 $\log_{10}$ copies/mL. All negative values were imputed to a value of 2.6 $\log_{10}$ copies/mL, which corresponds with a Ct-value of 40.

Blood for viral RNA load detection was collected from mice in two alternating sub-groups. Each sub-group comprised half of the mice (n/2=4) from each of the treatment groups (i) to (viii). Blood was collected from a first sub-group at days 2, 4, 6, 8 and 12 p.i. and from a second sub-group at days 3, 5, 7, 9 and 14 p.i. At day 12 p.i., half of the mice in each treatment group (n=4/group) were sacrificed. The remaining mice in each treatment group (n=4/group) were sacrificed at day 14 p.i. (FIG. 17Y).

Figure 17Z:
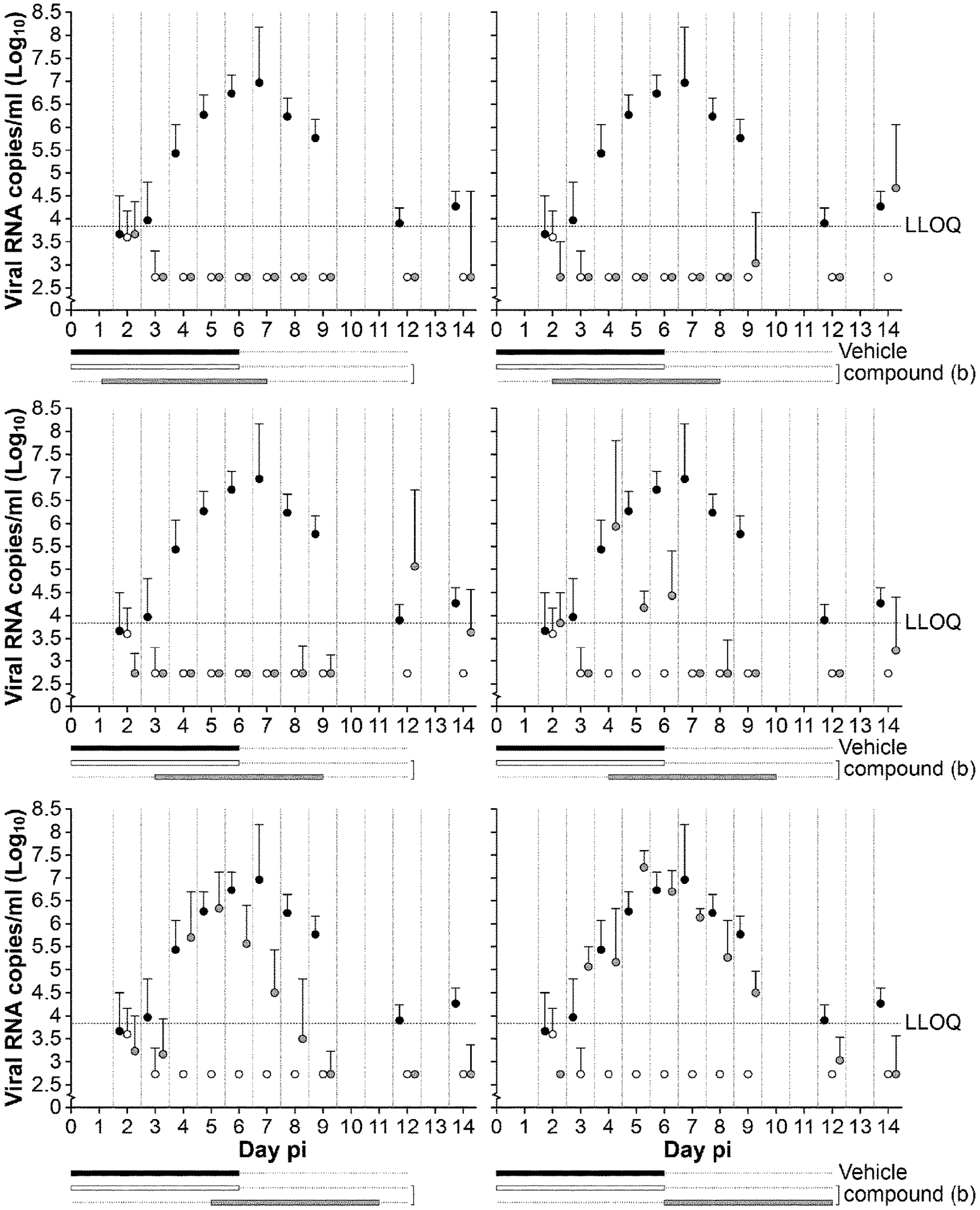

The vehicle-treated mice reached their peak viral load of 7.0 $log_{10}$ copies/mL at day 7 post infection. The viral RNA in the serum of mice belonging to groups 2, group 3 and group 4 was reduced to undetectable levels (below the imputed value of negative values of 2.6 $log_{10}$ copies/mL), except for two measurements in group 4, where a viral rebound was observed at day 9 (3.0 $log_{10}$ copies/mL) and day 14 (4.7 $log_{10}$ copies/mL) post infection (FIG. 15Z). In group 5, where treatment started at day 3 post infection and stopped at day 9 post-infection, undetectable viral load was observed until day 9 post infection, but viral RNA was detected (5.0 $log_{10}$ copies/mL) at day 12 post infection (FIG. 17Z).

In group 6 and group 7, peak viral load was still reduced with 1.1 and 0.7 $log_{10}$ copies/mL respectively. Compared with the vehicle treated mice, undetectable viral load was reached earlier for both treatment groups (FIG. 17Z).

This experiment further comprises an additional treatment group, i.e. group 8, in which the animals were treated with 30 mg/kg/dose of compound (b) b.i.d. The first administration of compound (b) took place 6 days after infection. In this group the peak viral load was similar to the vehicle treated group, but undetectable viral load was reached earlier than for the vehicle treated mice (FIG. 17Z).

The invention claimed is:

1. A method for the prevention of dengue in an individual at risk of being infected by Dengue virus or for the treatment of dengue disease in an individual infected by Dengue virus, comprising the step of administering to said individual a medicament comprising compound of formula I, wherein the first administration of the medicament occurs at least 24 hours prior to viral infection to at most 5 days after being infected, and wherein the formula I corresponds to

I

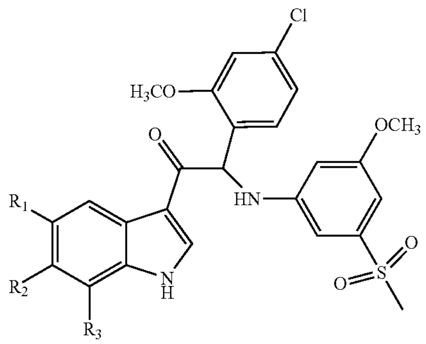

a stereo-isomeric form, a pharmaceutically acceptable salt, solvate or polymorph thereof; said compound is selected from the group wherein:
$R_1$ is H, $R_2$ is F and $R_3$ is H or $CH_3$,
$R_1$ is H, $CH_3$ or F, $R_2$ is $OCH_3$ and $R_3$ is H,
$R_1$ is H, $R_2$ is $OCH_3$ and $R_3$ is $CH_3$,
$R_1$ is $CH_3$, $R_2$ is F and $R_3$ is H,
$R_1$ is $CF_3$ or $OCF_3$, $R_2$ is H and $R_3$ is H,
$R_1$ is $OCF_3$, $R_2$ is $OCH_3$ and $R_3$ is H,
$R_1$ is $OCF_3$, $R_2$ is H and $R_3$ is $CH_3$.

2. The method according to claim 1, wherein the medicament is administered intermittently at least once every 24 hours.

3. The method according to claim 1, wherein the medicament comprises an effective amount of compound of formula I, said effective amount is selected such that dengue virus viral load in blood is kept at a level equal to or under 15 $log_{10}$ copies/mL.

4. The method according to claim 1, wherein the effective amount of the compound is from 0.05 mg/kg to 500 mg/kg body weight.

5. The method according to claim 1, wherein the medicament is administered orally, subcutaneously, intramuscularly, or intravenously.

6. The method according to claim 1, wherein the medicament is administered intermittently at least once every week.

7. The method according to claim 1, wherein the medicament is administered intermittently at least once every two weeks.

8. The method according to claim 1, wherein the medicament is administered intermittently at least once every month.

9. The method according to claim 1, wherein the medicament is administered intermittently at least once every 6 months.

10. The method according to claim 1, wherein the medicament comprises an effective amount of compound of formula I, said effective amount is selected such that dengue viral load in blood is kept at a level equal to or under 10 $\log_{10}$ copies/mL.

11. The method according to claim 1, wherein the medicament comprises an effective amount of compound of formula I, said effective amount is selected such that dengue viral load in blood is kept at a level equal to or under 7 $\log_{10}$ copies/mL.

12. The method according to claim 1, wherein the medicament comprises an effective amount of compound of formula I, said effective amount is selected such that dengue viral load in blood is kept at a level equal to or under 5 $\log_{10}$ copies/mL.

13. The method according to claim 1, wherein the medicament comprises an effective amount of compound of formula I, said effective amount is selected such that dengue viral load in blood is kept at a level equal to or under 3 $\log_{10}$ copies/mL.

14. The method according to claim 1, wherein the medicament comprises an effective amount of compound of formula I, said effective amount is selected such that dengue viral load in blood is kept at a level equal to or under 2 $\log_{10}$ copies/mL.

15. The method according to claim 1, wherein the compound is compound (a)

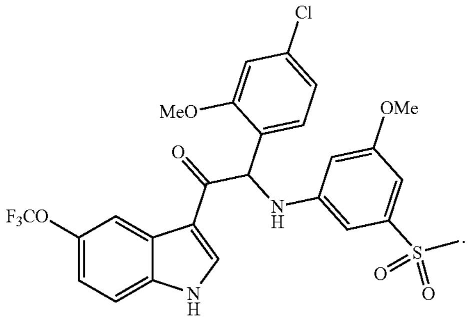

16. The method according to claim 15, wherein the compound is the (S)-enantiomer of the compound of formula (a).

* * * * *